United States Patent [19]
Chenchik et al.

[11] Patent Number: 5,565,340
[45] Date of Patent: Oct. 15, 1996

[54] METHOD FOR SUPPRESSING DNA FRAGMENT AMPLIFICATION DURING PCR

[75] Inventors: Alex Chenchik; Luda Diatchenko, both of Palo Alto; Paul Siebert, Sunnyvale, all of Calif.; Sergey Lukianov; Konstantin Lukianov, both of Moscow, U.S.S.R.; Nadia Gurskaya; Victor Tarabykin, both of Moscow, U.S.S.R.; Eugene Sverdlov, Moscow, U.S.S.R.

[73] Assignee: Clontech Laboratories, Inc., Palo Alto, Calif.

[21] Appl. No.: 381,572

[22] Filed: Jan. 27, 1995

[51] Int. Cl.$^6$ ............................ C07H 21/04; C12P 19/34; C12Q 1/68
[52] U.S. Cl. ............................ 435/91.2; 435/6; 435/7.1; 435/15; 435/91.1; 536/24.2; 536/24.3
[58] Field of Search .................... 435/91.1, 91.2, 435/7.1, 15, 6; 536/24.2, 24.33; 935/77, 78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,800,159 | 1/1989 | Mullis et al. | 435/122.3 |

OTHER PUBLICATIONS

Schlayler et al. J. Virol Meth. 38:333–341, 1992.
Apte et al. Biotechniques 15(5):890–893, 1993.
Lukianov, S. A. et al. (1994) "Highly Efficient Subtractive Hybridization of cDNA" Bioorganic Chemistry (Russia) 20(6):701–704.
Belyavsky, A. et al. (1989) "PCR-based cDNA library construction: general cDNA libraries at the level of a few cells" Nucleic Acids Research 17(8):2919–2932.
Brookes, A. J., D. J. Porteous (1991) "Coincident sequence clonging" Nucleic Acids Research 19(10):2609–2613.
Frohman, M. A. et al. (1988) "Rapid production of full-length cDNAs from rare transcripts: Amplification using a single gene-specific oligonucleotide primer" Proc. Natl. Acad. Sci. USA 85:8998–9002.
Hampson, I. N. et al. (1992) "Chemical cross linking subtraction (CCLS): a new method for the generation of subtractive hybridisation probes" Nucleic Acids Research 20(11):2899.
Hara, E. et al. (1993) "DNA–DNA subtractive cDNA Cloning Using oligo(dT)$_{30}$–Latex and PCR: identification of Cellular Genes Which are Overexpressed in Senescent Human–Diploid Fibroblasts".
Jones, D. H., S. C. Winistorfer (1993) "Genome Walking with 2-to 4-kb Steps Using Panhandle PCR" in PCR Methods and Applications (CSHL Press) 197–203.
Ko, M. S. H. (1990) "An 'equalized cDNA library' by the reassociation of short double-stranded cDNAs" Nucleic Acids Research 18(19):5705–5711.
Kellogg, D. E. et al. (1994) "TaqStart Antibody™: Hot Start PCR Facilitated by a Neutralizing Monoclonal Antibody directed Against Taq DNA Polymerase" BioTechniques 16(6):1134–1137.

(List continued on next page.)

Primary Examiner—Stephanie W. Zitomer
Assistant Examiner—Paul B. Tran
Attorney, Agent, or Firm—Saliwanchik & Saliwanchik

[57] ABSTRACT

The subject invention pertains to novel materials and methods for suppressing amplification of particular DNA fragments during polymerase chain reaction (PCR). The PCR suppression method uses novel adapters that are ligated to the end of a DNA fragment prior to PCR amplification. Upon melting and annealing, single-stranded DNA fragments having self-complementary adapters at the 5'- and 3'-ends of the strand can form suppressive "pan-like" double-stranded structures that suppress amplification of the fragments during PCR. The subject method offers improved specificity and sensitivity of PCR amplification of a target DNA and does not require target DNA sequence information. The subject invention can be adapted to a variety of highly useful PCR techniques and applications.

15 Claims, 6 Drawing Sheets

OTHER PUBLICATIONS

Lisitsyn, N. et al. (1993) "Cloning the Differences Between Two Complex Genomes" Science 259:946–951.

Riley, J. et al. (1990) "A novel, rapid method for the isolation of terminal sequences from yeast artificial chromosome (YAC) clones" Nucleic Acids Research 18(10):2887–2890.

Sverdlov, E. D. et al. (1993) "Subtractive Hybridization. Theoretical Analysis and a Principle of the <<Trapper>>" Bioorganic Chemistry (Russia) 19:1081–1088.

Timblin, C. et al. (1990) "Application for PCR technology to subtrctive cDNA cloning: identification of genes expressed specifically in murine plasmacytoma cells" Nucleic Acids Research 18(6):1587–1593.

Wang, Zhou, D. D. Brown (1991) "A gene expression screen" Proc. Natl. Acad. Sci. USA 88:11505–11509.

Saiki, R. K. et al. (1985) "Enzymatic Amplification of β–Globin Genomic Sequences and Restriction Site Analysis for Diagnosis of Sickle Cell Anemia" Science 230:1350–1354.

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 44 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:1:

```
TGTAAGCGTG AAGACGACAG AAAGGGCGTG GTGCGGAGGG CGGT                    44
```

( 2 ) INFORMATION FOR SEQ ID NO:2:

( i ) SEQUENCE CHARACTERISTICS:
        ( A ) LENGTH: 49 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

```
CGACGTGGAC TATCCATGAA CGCAACTCTC CGACCTCTCA CCGAGCGGT              49
```

( 2 ) INFORMATION FOR SEQ ID NO:3:

( i ) SEQUENCE CHARACTERISTICS:
    ( A ) LENGTH: 42 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:3:

CTCTGGCATC AACTCGGACT ATCTCTTCGT CATCTCACCA AG                    42

( 2 ) INFORMATION FOR SEQ ID NO:4:

( i ) SEQUENCE CHARACTERISTICS:
        ( A ) LENGTH: 48 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:4:

AGCACTCTCC AGCCTCTCAC CGCAATAGCG TGGTCTGCAG GGATGGGT              48

( 2 ) INFORMATION FOR SEQ ID NO:5:

( i ) SEQUENCE CHARACTERISTICS:
        ( A ) LENGTH: 44 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:5:

CTAATACGAC TCACTATAGG GCTCGAGCGG CCGCCCGGGC AGGT                  44

( 2 ) INFORMATION FOR SEQ ID NO:6:

( i ) SEQUENCE CHARACTERISTICS:
        ( A ) LENGTH: 44 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:6:

CTAATACGAC TCACTATAGG GCTCGAGCGG CCGCCCGGGC AGGT                  44

( 2 ) INFORMATION FOR SEQ ID NO:7:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:7:

AAGCAGCAGT GGTAACAACG CAGAG                                      25

( 2 ) INFORMATION FOR SEQ ID NO:8:

( i ) SEQUENCE CHARACTERISTICS:
        ( A ) LENGTH: 45 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:8:

AGCACTCTCC AGCCTCTCAC CGCAGTCGAC CGTTTTTTTT TTTTT 45

( 2 ) INFORMATION FOR SEQ ID NO:9:

( i ) SEQUENCE CHARACTERISTICS:
        ( A ) LENGTH: 47 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:9:

ACCGACGTGG ACTATCCATG AACGCAGTCG ACCGTTTTT TTTTTTT 47

( 2 ) INFORMATION FOR SEQ ID NO:10:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:10:

AGGGCGTGGT GCGGAGGGC 19

( 2 ) INFORMATION FOR SEQ ID NO:11:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:11:

ACTCTCCGAC CTCTCACCGA G 21

( 2 ) INFORMATION FOR SEQ ID NO:12:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:12:

CTCTGGCATC AACTCGGACT A 21

( 2 ) INFORMATION FOR SEQ ID NO:13:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:13:

AGCACTCTCC AGCCTCTCAC CGCA 24

(2) INFORMATION FOR SEQ ID NO:14:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:14:

TGTAAGCGTG AAGACGACAG AA 22

(2) INFORMATION FOR SEQ ID NO:15:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:15:

GGATCCTAAT ACGACTCACT ATAGGGC 27

(2) INFORMATION FOR SEQ ID NO:16:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:16:

AAGCAGCAGT GGTAACAACG CAGAG 25

(2) INFORMATION FOR SEQ ID NO:17:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:17:

TCGAGCGGCC GCCCGGGCAG GT 22

(2) INFORMATION FOR SEQ ID NO:18:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:18:

AATAGGGCTC GAGCGGC 17

(2) INFORMATION FOR SEQ ID NO:19:

( i ) SEQUENCE CHARACTERISTICS:
    ( A ) LENGTH: 24 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:19:

CGACGTGGAC TATCCATGAA CGCA                                      24

( 2 ) INFORMATION FOR SEQ ID NO:20:

( i ) SEQUENCE CHARACTERISTICS:
        ( A ) LENGTH: 50 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:20:

TTCTAGAATT CAGCGGCCGC TTTTTTTTTT TTTTTTTTTT TTTTTTTTTT           50

( 2 ) INFORMATION FOR SEQ ID NO:21:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:21:

AGAAACCCGA CCTACCACGG CTTGCTCCTT                                30

( 2 ) INFORMATION FOR SEQ ID NO:22:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:22:

CCCTTTCCTC GCAGAAATTT TCTCTCCAGC                                30

( 2 ) INFORMATION FOR SEQ ID NO:23:

( i ) SEQUENCE CHARACTERISTICS:
        ( A ) LENGTH: 35 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:23:

ACTCGTCATA CTCCTGCTTG CTGATCCACA TCTGC                          35

( 2 ) INFORMATION FOR SEQ ID NO:24:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear -continued (i i) MOLECULE TYPE: DNA (synthetic)

(x i) SEQUENCE DESCRIPTION: SEQ ID NO:24:

ACCTGACTGA CTACCTCATG AAGATCCTCA    30

(2) INFORMATION FOR SEQ ID NO:25:

(i) SEQUENCE CHARACTERISTICS:
(A) LENGTH: 26 bases
(B) TYPE: nucleic acid
(C) STRANDEDNESS: single
(D) TOPOLOGY: linear (i i) MOLECULE TYPE: DNA (synthetic)

(x i) SEQUENCE DESCRIPTION: SEQ ID NO:25:

GTCAATGTCC CAAACGTCAC CAGAGA    26

(2) INFORMATION FOR SEQ ID NO:26:

(i) SEQUENCE CHARACTERISTICS:
(A) LENGTH: 25 bases
(B) TYPE: nucleic acid
(C) STRANDEDNESS: single
(D) TOPOLOGY: linear (i i) MOLECULE TYPE: DNA (synthetic)

(x i) SEQUENCE DESCRIPTION: SEQ ID NO:26:

CTGCCAGCTT TACTGGAGAA CTTGA    25

METHOD FOR SUPPRESSING DNA FRAGMENT AMPLIFICATION DURING PCR

BACKGROUND OF THE INVENTION

Recently, a method for the enzymatic amplification of specific segments of DNA has been described. This method, known as polymerase chain reaction (PCR), is based on repeated cycles of denaturation of double-stranded DNA, followed by oligonucleotide primer annealing to the DNA template, and primer extension by a DNA polymerase (Mullis et al. U.S. Pat. Nos. 4,683,195, 4,683,202, and 4,800,159; Saiki et al. 1985). The oligonucleotide primers used in PCR are designed to anneal to opposite strands of the DNA, and are positioned so that the DNA polymerasecatalyzed extension product of one primer can serve as the template strand for the other primer. The PCR amplification process results in the exponential increase of discrete DNA fragments whose length is defined by the 5' ends of the oligonucleotide primers.

Application of PCR to isolate and analyze a particular DNA region requires knowledge of the DNA sequences flanking the region of interest. This generally limits amplification to regions of known DNA sequence. In the absence of the necessary sequence information, PCR amplification of a target DNA fraction in a complex DNA population is likely to result in the amplification of non-target DNA. Although methods have been developed to help overcome this problem, they have met with only limited success or application. These technologies have been used primarily for cloning populations of differentially expressed genes, for analyzing differences between two complex genomes (target DNA population) after subtractive hybridization of two complex DNA (or cDNA) mixtures, and for preparation of an "equalized cDNA library" (i.e., a cDNA library containing an equal abundance of all the cloned genes).

For selective amplification of target DNA, the target DNA is usually purified from non-target DNA using labor intensive and generally unreproducible physical separation techniques such as hydroxyapatite chromatography (Timblin et al., 1990; Ko, 1990), a streptavidin-biotin interaction (Wang et al., 1991) or oligo (dT)-latex beads (Hara et al., 1993). Another technique, known as "Coincidence Sequence Cloning," permits the selective amplification of common sequences shared between two complex and partially coincident DNA mixtures (Brookes et al., 1991). However, this procedure requires an M13 phage cloning procedure to produce the single-stranded DNA, as well as a preparative gel electrophoresis step to purify the "coincident sequences" before initiating the PCR amplification.

Techniques such as "chemical cross-linking subtraction" (Hampson et al., 1992), "vectorette" adapter technology (Riley et al., 1990) and "representational difference analysis" (Lisitsyn et al., 1993) have been developed which eliminate the physical separation step, thereby simplifying the technology for selective target amplification. However, "chemical cross-linking subtraction" can only be applied to mRNA-cDNA subtraction procedures and "vectorette" adapter technology requires knowledge of partial sequence information (the inner primer sequence) of the target DNA to be amplified. The highest efficiency of selective amplification of target DNA has been achieved using the simple "representational difference analysis" technique. This method is based on differences in the efficiency of exponential amplification of target DNA and the linear amplification of non-target DNA through the use of a special adapter design.

In view of the problems and limitations associated with each of the amplification methods discussed above, there remains a need for a method of enhancing the specificity and sensitivity of target DNA amplification. Such a method has been described, in part, by Lukianov et al., 1994. Application of the subject invention during PCR efficiently suppresses non-target DNA amplification while allowing for the exponential amplification of target DNA sequences.

BRIEF DESCRIPTION OF THE INVENTION

The subject invention pertains to a unique method for the efficient suppression of DNA fragment amplification during polymerase chain reaction (PCR). In a preferred embodiment, the method of the subject invention uses a double-stranded adapter that is attached to each end of a target double-stranded DNA fragment. The adapter comprises an "outer" complementary primer binding sequence portion and an "inner" suppressor sequence portion.

The suppression method of the subject invention uses a PCR primer which is shorter in length than the adapter and is capable of hybridizing to the primer binding portion of the adapter. Upon initiation of PCR after the denaturation step, the single-stranded DNA (ssDNA) fragment bearing the complementary single-stranded portion of the adapters at each end of the ssDNA fragment may form either a self-annealing "pan-like" structure (amplification suppressive structure) or a DNA/primer "hybrid" structure (amplification permissive structure). The relative ratio of formation of the two structures using the subject method during PCR cycling depends on a number of factors, including the differences between the melting temperatures of the suppressive and permissive structures, the position of the complementary primer binding site within the adapter sequence, and the size of the DNA fragment to be amplified. Using the teachings provided herein, these factors can be manipulated to achieve the desired suppression of non-target DNA during PCR amplification.

The method according to the subject invention can be used for the selective amplification of target DNA fragments in a complex DNA mixture and can also be used to selectively control the size of PCR products which can be amplified in a reaction. The subject invention is particularly suitable for use with a variety of PCR and molecular biology applications.

The subject invention also pertains to novel adapters used with the PCR suppression method of the subject invention. In addition to the adapters specifically exemplified, a wide variety of adapters for use with the subject method can be readily prepared using the teachings disclosed herein.

BRIEF DESCRIPTION OF THE SEQUENCE

Figure 1:
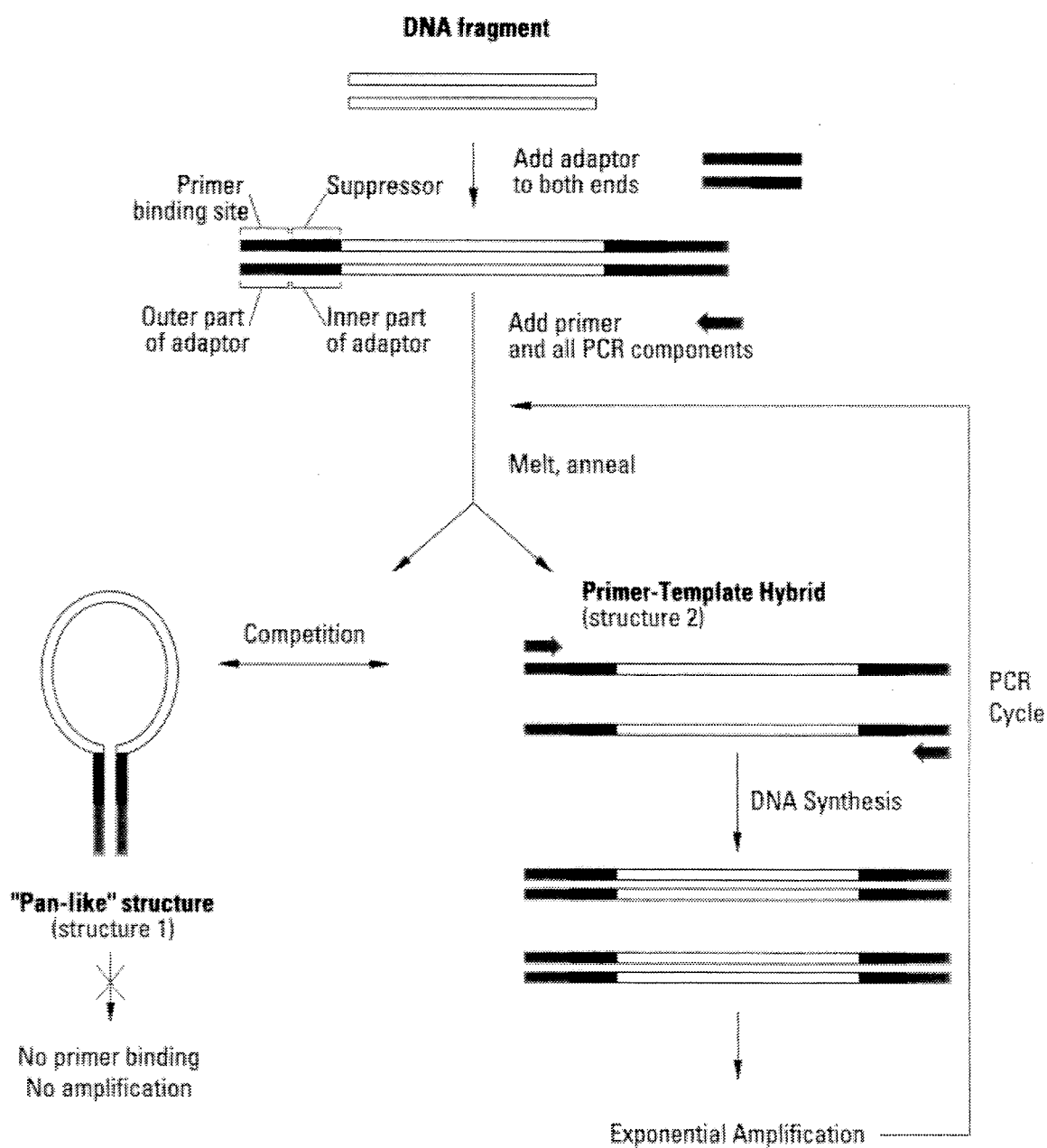
FIG. 1 shows a schematic representation of the general PCR suppression mechanism of the subject invention.

The SEQ ID NO. for the nucleotide sequence of the adapters corresponds to the nucleotide sequence of the upper nucleotide strand shown in Table 1.

SEQ ID NO. 1 is the nucleotide sequence of the adapter Na 21-St19.

SEQ ID NO. 2 is the nucleotide sequence of the adapter Lu4-St11.

SEQ ID NO. 3 is the nucleotide sequence of the adapter Na 23-St7.

SEQ ID NO. 4 is the nucleotide sequence of the adapter Lu3-St24.

SEQ ID NO. 5 is the nucleotide sequence of the adapter T7-NotSrf.

SEQ ID NO. 6 is the nucleotide sequence of the adapter T7-NotSffA.

SEQ ID NO. 7 is the nucleotide sequence of the adapter Ad1SGT.

SEQ ID NO. 8 is the nucleotide sequence of the adapter Lu3-T13.

SEQ ID NO. 9 is the nucleotide sequence of the adapter Lu4-T13.

SEQ ID NO. 10 is the nucleotide sequence of the primer St19.

SEQ ID NO. 11 is the nucleotide sequence of the primer St1.

SEQ ID NO. 12 is the nucleotide sequence of the primer Na23.

SEQ ID NO. 13 is the nucleotide sequence of the primer Lu3.

SEQ ID NO. 14 is the nucleotide sequence of the primer Na21.

SEQ ID NO. 15 is the nucleotide sequence of the primer T7.

SEQ ID NO. 16 is the nucleotide sequence of the primer Na1SGT.

SEQ ID NO. 17 is the nucleotide sequence of the primer NotSrf1.

SEQ ID NO. 18 is the nucleotide sequence of the primer NotSrf4.

SEQ ID NO. 19 is the nucleotide sequence of the primer Lu4.

SEQ ID NO. 20 is the nucleotide sequence of the primer RI-Not-T30.

SEQ ID NO. 21 is the nucleotide sequence of the primer TPA1.

SEQ ID NO. 22 is the nucleotide sequence of the primer

SEQ ID NO. 23 is the nucleotide sequence of the primer for 5'-RACE for human beta-actin gene.

SEQ ID NO. 24 is the nucleotide sequence of the primer for 3'-RACE for human beta-actin gene.

SEQ ID NO. 25 is the nucleotide sequence of the primer for 5'-RACE of human transferin receptor gene.

SEQ ID NO. 26 is the nucleotide sequence of the primer for 3'-RACE of human transferin receptor gene.

DETAILED DESCRIPTION OF THE INVENTION

The subject invention concerns a novel method for the selective suppression of polymerase chain reaction (PCR) amplification of DNA fragments. In accordance with a preferred embodiment, the DNA fragments whose amplification by PCR is to be regulated according to the methods of the subject invention have the same double-stranded adapter attached at each end of the fragment. The adapter used according to the subject invention comprises a polynucleotide sequence that includes a primer binding portion and a suppressor sequence portion. After attachment of the adapters to the DNA fragments and filling in the ends to eliminate any single-strandedness, each strand of the DNA fragment has an adapter sequence at its 5'-end that is complementary to the adapter sequence at its 3'-end. As an initial step in the PCR procedure, the DNA fragments are denatured to yield single-stranded DNA. In the next step of standard PCR, primers are allowed to anneal to the single-stranded DNA. During the primer annealing phase of the subject PCR method, a single-stranded DNA fragment bearing the complementary sequences at each end can hybridize with itself through the complementary adapter sequences to form a secondary structure that blocks the amplification of that DNA fragment. However, DNA fragments in a DNA mixture which have different adapters attached at each end (and thus, the ends of the single-stranded DNA fragment are not self-complementary) can be exponentially amplified as usual during PCR using a combination of primers which can hybridize with the adapters and function in primer extension.

After the first round of denaturation and annealing in the PCR procedure of the subject invention, each strand of a DNA fragment can form either a self-annealing "pan-like" structure (amplification suppressive structure), or it can form a "hybrid" structure comprising the single-stranded DNA and the PCR primer (amplification permissive structure). The "pan-like" structure will form if complementary adapter sequences are present at each end of a single DNA strand and those sequences hybridize to each other. When hybridization of the adapter sequences occurs, a closed loop is formed (the "pan-like" suppressive structure) and amplification is prevented or inhibited. Alternatively, a PCR primer may hybridize with the single-stranded adapter (the amplification permissive "hybrid" structure), in which case amplification can proceed according to the standard PCR procedure. If a single-stranded DNA fragment bears an adapter sequence at its 5'-end that is not complementary to the adapter sequence found at the 3'-end of that same strand, then the "pan-like" suppressive structure cannot be formed and those DNA fragments can be efficiently amplified in a PCR reaction using appropriate primers that hybridize to the adapter sequence or to the DNA fragment. Accordingly, the skilled artisan can use the subject invention with PCR to amplify target DNA fragments, while non-target DNA fragment amplification is suppressed. The basic methodology of the subject invention, including the formation of the "pan-like" and "hybrid" structures, is illustrated in FIG. 1.

As used herein, the term "target" DNA or nucleic acid refers to that polynucleotide material to be amplified in the DNA or nucleic acid sample. The term "non-target" refers to that polynucleotide material for which amplification is not desired. A DNA fragment in a sample is either a "target" or a "non-target" DNA. The determination of whether a DNA fragment is a "target" or a "non-target" is independent of whether the adapters of the subject invention are attached to the DNA fragment.

For those DNA fragments that have the complementary adapter sequences of the subject invention at each end, the relative ratio of formation of the two types of structures is dependent upon a number of factors that can shift the balance to favor the formation of one structure over the other. The manipulation of these factors to achieve the desired, selective PCR suppression is a critical aspect of the subject invention.

The equilibrium constant associated with the formation of the suppressive and the permissive structures, and, therefore, the efficiency of suppression of particular DNA fragments during PCR, is primarily a function of the following factors:

(a) Differences in melting temperature of suppressive and permissive structures. If the suppressor sequence portion of the adapter is roughly equal to or longer than the primer binding portion, then the suppressive structure will be preferentially formed due to the higher melting temperatures of the suppressive structure versus the permissive structure. If the suppressor portion is about one half, or less, the length of the primer binding portion, or is absent altogether, then the amplification permissive structure typically will be formed and those DNA fragments can be efficiently amplified under standard PCR amplification reaction conditions. The permissive structure is particularly preferred at higher primer concentrations. In addition to sequence length, the differences in melting temperatures of the suppressive and permissive structures are also determined by the relative ratio of guanosine and cytidine residues to adenosine and thymidine residues (hereinafter this ratio is referred to as the GC content of the sequence) in the primer binding and suppressor sequence portion of the adapter. For an adapter having a primer binding portion and a suppressor portion of fixed length, the higher the GC content of the suppressor portion, the greater the efficiency of suppression that can be achieved (using the same primer binding portion of the adapter). Thus, in order to achieve similar efficiencies of suppression for various adapters having suppressor and primer binding portions of approximately equal length, the primer binding and suppressor portions of the adapter should contain approximately equal GC content (assuming all other conditions are held constant).

(b) Position of primer sequence within an adapter. The PCR suppression mechanism of the subject invention works most efficiently when primers are used which are complementary to the primer binding portion of the adapter (i.e., the outer or distal part of the adapter) on the 3'-end of the single-stranded DNA fragment. This results in the replication of the complete suppressor sequence portion of the adapter after primer extensions. The presence of suppressor sequence permits the suppressive structure to be readily formed again after each round of denaturation during PCR. In contrast, the use of PCR primers which are complementary to the suppressor portion of the adapter (i.e., the inner or proximal part of the adapter) results in a shorter amplification product that lacks an outer portion of the adapter after the first round of amplification. Because these shorter PCR products lack an outer portion of the adapter, they have a reduced ability to form the "pan-like" suppressive structure. These shorter amplification products can then be efficiently amplified in all subsequent PCR cycles using the primer that is complementary to the suppressor portion of the adapter.

(c) Length of the target DNA fragments. The longer the target DNA fragment, the greater the distance between the complementary sequences at the 5'- and 3'-ends of the single-stranded DNA fragment, and the less efficiently a suppressive structure can be formed. Accordingly, the efficiency of the PCR suppression of the subject invention is reduced for larger target DNA fragments. When standard-sized primers (typically about 21–24 nucleotides in length) are used in conjunction with an adapter having a suppressor sequence of about the same length, PCR amplification of DNA fragments of up to about 6–8 kb in length can be effectively suppressed.

(d) PCR primer concentration. The suppression effect achieved according to the methods of the subject invention works more efficiently at lower primer concentrations (typically from about 0.1 µM to about 0.2 µM) than at higher primer concentrations (typically from about 0.5 µM to about 1.0 µM). In addition, the size of the DNA fragments which can be efficiently amplified (or suppressed) also depends on the primer concentration. If the primer concentration is increased (e.g., from about 0.1 µM to about 1.0 µM), the ability to suppress PCR amplification of larger fragments is decreased and, therefore, the size border between amplified and suppressed fractions is shifted downward.

(e) Primary structure. The primary structure of the PCR primer binding and suppressor portions of the adapter also influence the efficiency of suppression, but to a lesser extent than the other factors.

In addition to the unique PCR suppression method described herein, the subject invention further concerns the novel polynucleotide adapters used with the subject method. These adapters have a unique sequence design which comprises an "outer" primer binding sequence portion and an "inner" suppressor sequence portion. As used herein, the term "outer" refers to that portion of the adapter sequence that is distal to the DNA fragment to which it is attached. The term "inner" refers to that portion of the adapter sequence that is proximal to the DNA fragment to which it is attached.

The adapters can be composed of either DNA or RNA and can be either single-stranded or double-stranded when attached to the DNA fragment. In a preferred embodiment, the adapters are at least partially double-stranded to aid in ligation of the adapter to the DNA fragment. The adapters can be attached to the ends of DNA or RNA fragments using a variety of techniques that are well known in the art, including DNA ligase-mediated ligation of the adapters to sticky- or blunt-ended DNA, T4 RNA ligase-mediated ligation of a single-stranded adapter to single-stranded RNA or DNA, oligo (dA) tailing using terminal transferase, or via any DNA polymerase (or a reverse transcriptase if RNA is the template) using a primer having a sequence which corresponds to the adapter sequence. As used herein, the term "attach," when used in the context of attaching the adapter to a DNA fragment, refers to bringing the adapter into covalent association with the DNA fragment regardless of the manner or method by which the association is achieved.

Alternatively, DNA fragments can be cloned into plasmid vectors that have the adapters of the subject invention inserted in the appropriate orientation upstream and downstream of a cloning site in the vector. In this case, the adapters per se consist of a single vector sequence in the plasmid that duplicates the adapter sequence upstream and downstream from a cloning site. The vector can include any plasmid sequence that is necessary for maintenance of the recombinant DNA in a host cell.

Several types of adapter structures are contemplated for use with the subject invention. Two types of adapters are specifically exemplified and are referred to herein as "Type 1" and "Type 2" adapter structures. Using the teachings contained herein, the skilled artisan could readily construct other adapters that have different sequences from those adapters exemplified herein, including variants of the subject adapters, that would be operable with the subject invention. Any polynucleotide sequence that comprises a primer binding portion and an effective suppressor sequence portion and which when associated with a DNA or RNA fragment can form a suppressive "pan-like" structure during PCR as described herein is contemplated by the subject invention. Such adapters are within the scope of the subject invention.

The Type 1 adapter structure typically has a length of about 42–50 nucleotides. However, the adapter length can vary from as few as about 25 nucleotides, up to 80 or more nucleotides. Generally, the Type 1 adapter does not contain any homopolymer sequence. The Type 1 adapter is typically at least partially double-stranded and generally comprises one long oligomer and one short oligomer, resulting in a 5' overhang at one end of the adapter. The typical structure for a Type 1 adapter and its corresponding primer are illustrated by the T7-NotSrf adapter (SEQ ID NO. 5) and the T7 primer (SEQ ID NO. 15). The length of the lower oligomer is not critical to the function of the PCR suppression method of the subject invention. The lower oligomer can be shorter, equal to, or longer in length than the upper oligomer.

The design of the Type 1 adapter allows it to be ligated to any blunt-ended DNA fragment using T4 DNA ligase. Adapters having "sticky ends" that are compatible with certain restriction sites can also be used to attach the adapter to DNA that has been digested with appropriate restriction endonucleases. In most instances, only the upper (and typically longer) oligomer of the adapter can be ligated to DNA. The lower (and typically shorter) oligomer usually is not ligated because it lacks the requisite 5'-phosphate group. However, the lower oligomer portion of the adapter does increase the efficiency of ligation of the adapter to double-stranded DNA (dsDNA). In those instances where it is desirable to do so, it is possible to modify the lower oligomer so that it can be ligated to the DNA fragment. Typically, these modifications include adding a 5'-phosphate for more efficient ligation. Additionally, a 3'-amine group can be incorporated into the adaptor to prevent extension of the 3'-end of the lower oligomer, thus preventing the formation of the primer binding site on the general population of adapter-ligated DNA fragments.

The specific design of the Type 1 adapter can be manipulated in accordance with the teachings provided herein to achieve desired levels of PCR suppression for particular applications of this technology. The efficiency of the suppression observed using different Type 1 adapters is primarily a function of:

(a) The length of the suppressor portion of the adapter structure. The longer the suppressor portion, the more efficient the suppression when used in conjunction with the same primer binding portion of the adapter.

(b) The melting temperature of the suppressor portion. The higher the melting temperature, the higher the efficiency of suppression. Higher melting temperatures can be achieved, for example, by increasing the GC content of a particular sequence.

(c) Generally, the length of the primer used with the subject invention is directly proportional to the length of the suppressor portion of the adapter. Thus, the shorter the primer used during PCR, the shorter the suppressor sequence required to achieve a particular level of suppression (assuming that the relative GC content and sequence of the adapter is maintained).

(d) The nucleotide sequence of the adapter. Substitution of nucleotides in the adapter sequence (even as few as 2–3 bases), especially in that region of the adapter where the primer binding portion joins the suppressor portion, can lead to changes in the efficiency of PCR suppression. However, this factor is not as critical to the efficiency of suppression as are the length or GC content of the primer binding and suppressor portions of the adapter.

Thus, the efficiency of suppression can be regulated through varying the length and GC content (which in turn determines the melting temperature of the dsDNA) of the suppressor portion of the adapter.

The Type 2 adapter structure is similar to the Type 1 structure but contains a homopolymer sequence in the suppressor portion of the adapter. Typically, the Type 2 adapter is incorporated into DNA fragments that have been tailed with oligo (dA) using terminal deoxynucleotidyl transferase, followed by PCR using a primer such as Lu3-T13 (SEQ ID NO. 8). In this case, the primer becomes incorporated into the DNA as an adapter. The PCR product can be subsequently treated with exonuclease III to remove the lower strand of the adapter.

The skilled artisan will readily recognize that certain of the primers of the subject invention can also be used as adapters. For example, the Lu3-T13 (SEQ ID NO. 8) and Lu4-T13 (SEQ ID NO. 9) primers can also function as adapters in certain PCR protocols performed using the subject invention. The use of the subject primers as adapters in the subject method, and vice versa, is contemplated by the subject invention.

Preferably, the adapter should not contain any sequences that can result in the formation of "hairpins" or other secondary structures in the DNA which can prevent adapter ligation or primer extension. As would be readily apparent to a person skilled in the art, the primer binding sequence portion of the adapter can be complementary with a PCR primer capable of priming for PCR amplification of a target DNA.

Preferably, the primers of the subject invention have exact complementarity with the adapter sequence. However, primers used in the subject invention can have less than exact complementarity with the primer binding sequence of the adapter as long as the primer can hybridize sufficiently with the adapter sequence so as to be extendable by a DNA polymerase. As used herein, the term "primer" has the conventional meaning associated with it in standard PCR procedures, i.e., an oligonucleotide that can hybridize to a polynucleotide template and act as a point of initiation for the synthesis of a primer extension product that is complementary to the template strand.

The adapters and primers used in the subject invention can be readily prepared by the skilled artisan using a variety of techniques and procedures. For example, adapters and primers can be synthesized using a DNA or RNA synthesizer. In addition, adapters and primers may be obtained from a biological source, such as through a restriction enzyme digestion of isolated DNA. The primers can be either single- or double-stranded. Preferably, the primers are single stranded. The primer and adapters specifically exemplified herein are shown in Table 1.

TABLE 1

| | |
|---|---|
| ADAPTER Na21-St19 (SEQ ID NO. 1) | 5' - TGTAAGCGTGAAGACGACAGAAAGGGCGTGGTGCGGAGGGCGGT - 3'<br>3' - GCCTCCCGCCA - 5' |
| ADAPTER Lu4-St11 (SEQ ID NO. 2) | 5' - CGACGTGGACTATCCATGAACGCAACTCTCCGACCTCTCACCGAGCGGT - 3'<br>3' - GGCTCGCCA - 5' |
| ADAPTER Na23-St7 (SEQ ID NO. 3) | 5' - CTCTGGCATCAACTCGGACTATCTCTTCGTCATCTCACCAAG - 3'<br>3' - AGTAGAGTGGTTC - 5' |
| ADAPTER Lu3-St24 (SEQ ID NO. 4) | 5' - AGCACTCTCCAGCCTCTCACCGCAATAGCGTGGTCTGCAGGGATGGGT - 3'<br>3' - CCCTACCCA - 5' |
| ADAPTER T7-NotSrf (SEQ ID NO. 5) | 5' - CTAATACGACTCACTATAGGGCTCGAGCGGCCGCCCGGGCAGGT - 3'<br>3' - CCCGTCCA - 5' |
| ADAPTER T7-NotSrfA (SEQ ID NO. 6) | 5' - CTAATACGACTCACTATAGGGCTCGAGCGGCCGCCCGGGCAGGT - 3'<br>3' - TTATGCTGAGTGATATCCCGAGCTCGCCGGCGGGCCCGTCCA - 5' |
| ADAPTER Ad1SGT (SEQ ID NO. 7) | 5' - AAGCAGCAGTGGTAACAACGCAGAG - 3'<br>3' - TCGTCACCATTGTTGCGTCTC - 5' |
| PRIMER St19 (SEQ ID NO. 10) | 5' - AGGGCGTGGTGCGGAGGGC - 3' |
| PRIMER St1 (SEQ ID NO. 11) | 5' - ACTCTCCGACCTCTCACCGAG - 3' |
| PRIMER Na23 (SEQ ID NO. 12) | 5' - CTCTGGCATCAACTCGGACTA - 3' |
| PRIMER Na21 (SEQ ID NO. 14) | 5' - TGTAAGCGTGAAGACGACAGAA - 3' |
| PRIMER T7 (SEQ ID NO. 15) | 5' - GGATCCTAATACGACTCACTATAGGGC - 3' |
| PRIMER TPA 1 (SEQ ID NO. 21) | 5' - AGAAACCCGACCTACCACGGCTTGCTCCTT - 3' |
| PRIMER TPA 2 (SEQ ID NO. 22) | 5' - CCCTTTCCTCGCAGAAATTTTCTCTCCAGC - 3' |
| PRIMER NotSrf1 (SEQ ID NO. 17) | 5' - TCGAGCGGCCGCCCGGGCAGGT - 3' |
| PRIMER NotSrf 4 (SEQ ID NO. 18) | 5' - AATAGGGCTCGAGCGGC - 3' |
| PRIMER Lu3 (SEQ ID NO. 13) | 5' - AGCACTCTCCAGCCTCTCACCGCA - 3' |
| PRIMER Lu3-T13 (SEQ ID NO. 8) | 5' - AGCACTCTCCAGCCTCTCACCGCAGTCGACCGTTTTTTTTTTTTT - 3' |
| PRIMER Lu4 (SEQ ID NO. 19) | 5' - CGACGTGGACTATCCATGAACGCA - 3' |
| PRIMER Lu4-T13 (SEQ ID NO. 9) | 5' - ACCGACGTGGACTATCCATGAACGCAGTCGACCGTTTTTTTTTTTTT - 3' |
| PRIMER Na1SGT (SEQ ID NO. 16) | 5' - AAGCAGCAGTGGTAACAACGCAGAG - 3' |
| 5'-RACE Human beta-actin primer (SEQ ID NO. 23) | 5' - ACTCGTCATACTCCTGCTTGCTGATCCACATCTGC - 3' |
| 3'-RACE Human beta-actin primer (SEQ ID NO. 24) | 5' - ACCTGACTGACTACCTCATGAAGATCCTCA - 3' |
| 5'-RACE Human transferin receptor primer (SEQ ID NO. 25) | 5' - GTCAATGTCCCAAACGTCACCAGAGA - 3' |
| 3'-RACE Human | 5' - CTGCCAGCTTTACTGGAGAACTTGA - 3' |

TABLE 1-continued transferin receptor
primer
(SEQ ID NO. 26)
PRIMER RI-Not-T30    5' - TTCTAGAATTCAGCGGCCGCTTTTTTTTTTTTTTTTTTTTTTTTTTTTTT - 3'
(SEQ ID NO. 20)

---

The subject invention further concerns kits which contain, in separate packaging or compartments, the reagents such as adapters and primers required for practicing the PCR suppression method of the subject invention. Such kits may optionally include the reagents required for performing PCR reactions, such as DNA polymerase, DNA polymerase cofactors, and deoxyribonucleotide-5'-triphosphates. Optionally, the kit may also include various polynucleotide molecules, DNA or RNA ligases, restriction endonucleases, reverse transcriptases, terminal transferases, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure.

A variety of DNA polymerases can be used during PCR with the subject invention. Preferably, the polymerase is a thermostable DNA polymerase such as may be obtained from a variety of bacterial species, including *Thermus aquaticus* (Taq), *Thermus thermophilus* (Tth), *Thermus filiformis, Thermus flavus, Thermococcus literalis,* and *Pyrococcus furiosus* (Pfu). Many of these polymerases may be isolated from the bacterium itself or obtained commercially. Polymerases to be used with the subject invention can also be obtained from cells which express high levels of the cloned genes encoding the polymerase.

The subject invention can also be used with long distance (LD) PCR technology (Barnes, 1994; Cheng et al., 1994). LD PCR, which uses a combination of thermostable DNA polymerases, produces much longer PCR products with increased fidelity to the original template as compared to conventional PCR performed using Taq DNA polymerase alone.

The method of the subject invention can also be used in conjunction with antibodies that bind to DNA polymerase and thereby inhibit polymerase function (Kellogg et al., 1994). These antibodies reversibly bind to DNA polymerase in a temperature-specific manner, and thereby increase the specificity of a PCR reaction by inhibiting the formation of non-specific amplification products prior to initiation of PCR amplification.

The subject method can be used with polynucleotides comprising either full-length RNA or DNA, or their fragments. The RNA or DNA can be either double-stranded or single-stranded, and can be in a purified or unpurified form. Preferably, the polynucleotides are comprised of DNA. The DNA fragments used in the subject invention can be obtained from DNA by random sheafing of the DNA, by digestion of DNA or cDNA with restriction endonucleases, or by amplification of DNA fractions from DNA using arbitrary or sequence-specific PCR primers. The subject invention can also be used with full-size cDNA polynucleotide sequences, such as can be obtained by reverse transcription of RNA. The DNA can be obtained from a variety of sources, including both natural and synthetic sources. The DNA can be from any natural source including viruses, bacteria, yeast, plants, insects and animals. The DNA can also be prepared from any RNA source.

The PCR suppression methods of the subject invention can be used in a wide variety of procedures. Several of these procedures are specifically exemplified herein. Other procedures would become apparent to one skilled in the an having the benefit of this disclosure.

Figure 2:
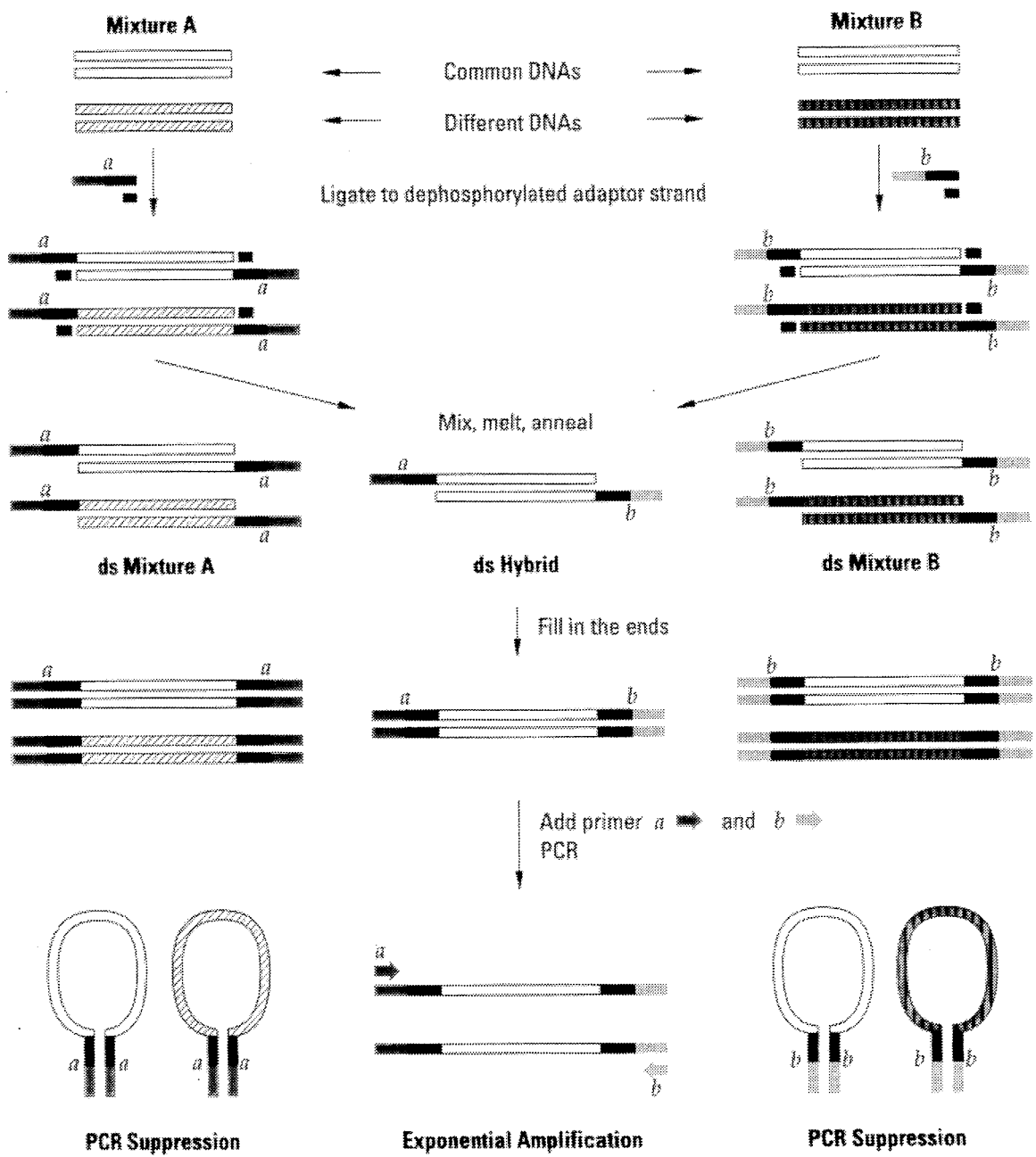
FIG. 2 shows a schematic representation of the selective amplification of DNA sequences that are common to two different DNA mixtures using the subject invention.

In one embodiment, the subject invention can be used for the selective recovery of DNA sequences common to two complex, partially homologous DNA mixtures. A schematic representation of the subject invention as applied to a pair of separate DNA mixtures (A and B) is illustrated in FIG. 2. DNA fragments from mixture A are ligated to adapter a, whereas DNA fragments from mixture B are ligated to adapter b. Adapters a and b have sequences that are non-complementary to each other (i.e., a strand from adapter a will not hybridize with a strand from adapter b). Mixture A and mixture B are combined, denatured, and then allowed to anneal in a reaction driven essentially to completion by all components. Single-stranded DNA fragments from mixtures A and B that have sufficient homology can re-anneal to form a double-stranded DNA fragment that has adapter a attached at one end and adapter b attached at its other end. After filling in the overhanging single-stranded ends of the fragments, the homologous species are selectively recovered from this mixture by PCR amplification using DNA primers complementary to the outer primer binding portion of adapter a and adapter b. The lack of complementarity between adapter a and adapter b prevents the formation of the suppressive "pan-like" structure in the DNA fragments bearing each of the a and b adapters. These DNA fragments that have both adapter a and adapter b attached can be efficiently amplified by PCR using primers complementary to the primer binding portion of adapters a and b. DNA from mixture A and mixture B that is not sufficiently homologous cannot be efficiently amplified since those fragments have complementary adapter sequences (a or b) at the 5' and 3' ends of each single-stranded DNA which then permits the formation of the PCR suppressive "pan-like" structure. In this embodiment, the subject invention can be applied to search for homology between different genomic DNAs and to reveal common sequences between different cDNAs (or RNAs). The subject invention can also be used to clone transcriptionally active regions in genomic DNA using a DNA-cDNA hybridization approach.

The subject invention can also be used to identify and isolate common sequences between genomic DNA and any particular fragment of genomic DNA (or cDNA) cloned into plasmid, phage, viral, cosmid or YAC vectors. This approach can be applied to mapping chromosome aberrations (point mutations, deletions, insertions, transversions, etc.) in patients with certain hereditary diseases using cytogenetic chromosome mapping data and a set of recombinant vectors which contain DNA fragments covering the disease target region.

Figure 3:
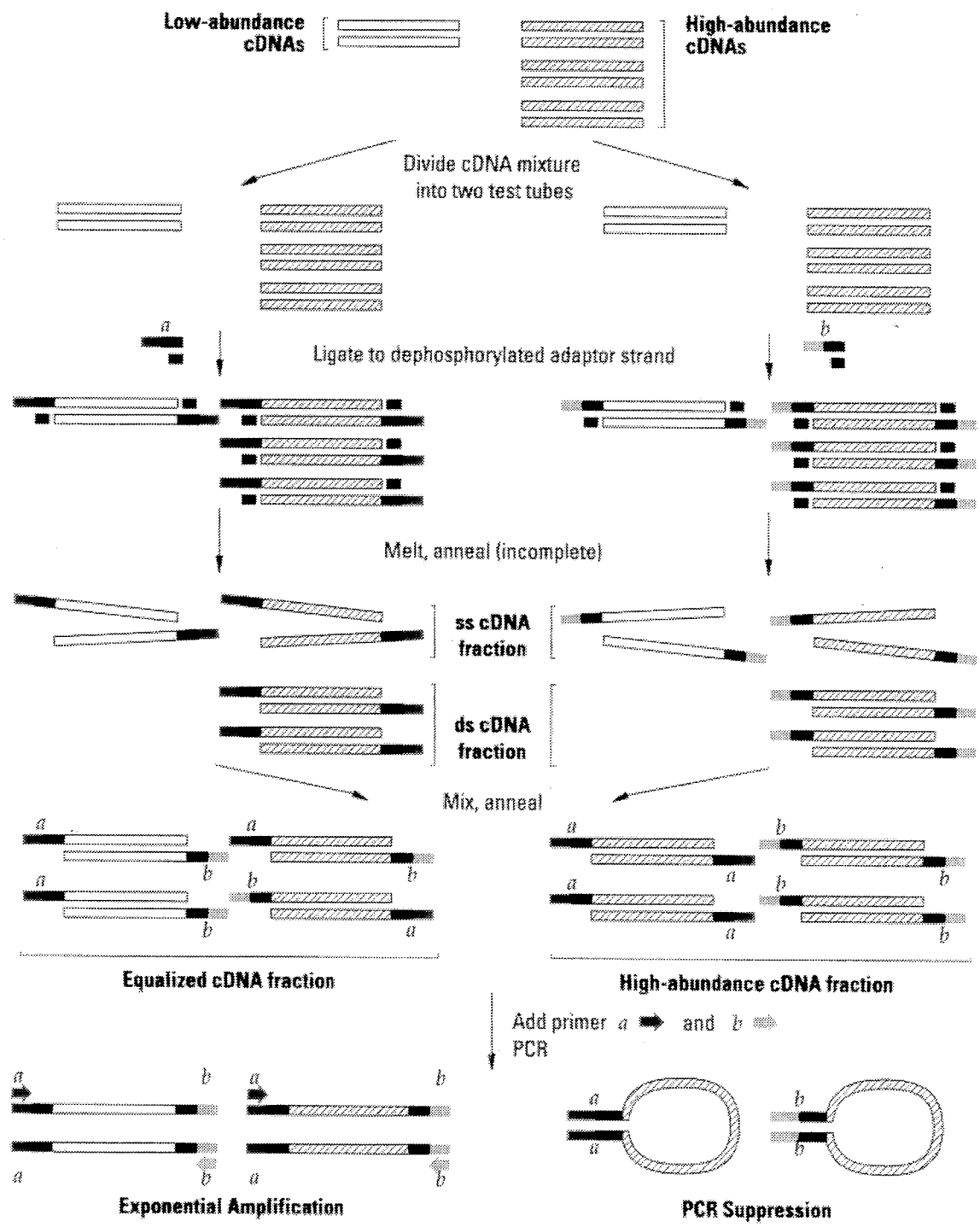
FIG. 3 shows a schematic representation of the preparation of a uniform-abundance cDNA population using the subject invention.

The subject invention can also be used to make a uniform-abundance ("equalized" or "normalized") cDNA population that contains approximately equal representation of each cDNA present in a sample. Double-stranded cDNA is split into two samples, and then the DNA in each sample is ligated to a different adapter (a or b) in separate test tubes as illustrated in FIG. 3. Optionally, the adapters may lack a phosphate on the 5'-ends of the shorter oligonucleotide; therefore, only the longer oligonucleotide of the adapter can be ligated to the cDNA. After melting and a brief re-annealing (which is not carried out to completion), the remaining single-stranded fraction in each sample is significantly depleted of the more abundant species of cDNA because the rate of re-annealing is proportional to the concentration of individual cDNAs in solution. The contents of the two test tubes are then mixed together, and hybridization is continued in order to re-anneal the equalized single-stranded fraction. The overhanging single-stranded ends of the double-stranded DNA fragments can then be filled in using a DNA polymerase, such as Taq DNA polymerase.

As a result of this procedure, only the equalized fraction of cDNA contains different adapters at both ends of the cDNA strand. These equalized cDNA fragments can be exponentially amplified using a combination of primers complementary to the primer binding portions of each adapter. Highly abundant cDNA fragments will have the same adapter (a or b) attached at each end because they re-annealed prior to mixing the two samples together. These cDNAs cannot be efficiently amplified because they can form the suppressive "pan-like" structure. After PCR amplification using primers complementary to the primer binding portion of adapters a and b, the cDNA consists of roughly equal amounts of each individual cDNA present in the original cDNA population.

Figure 4:
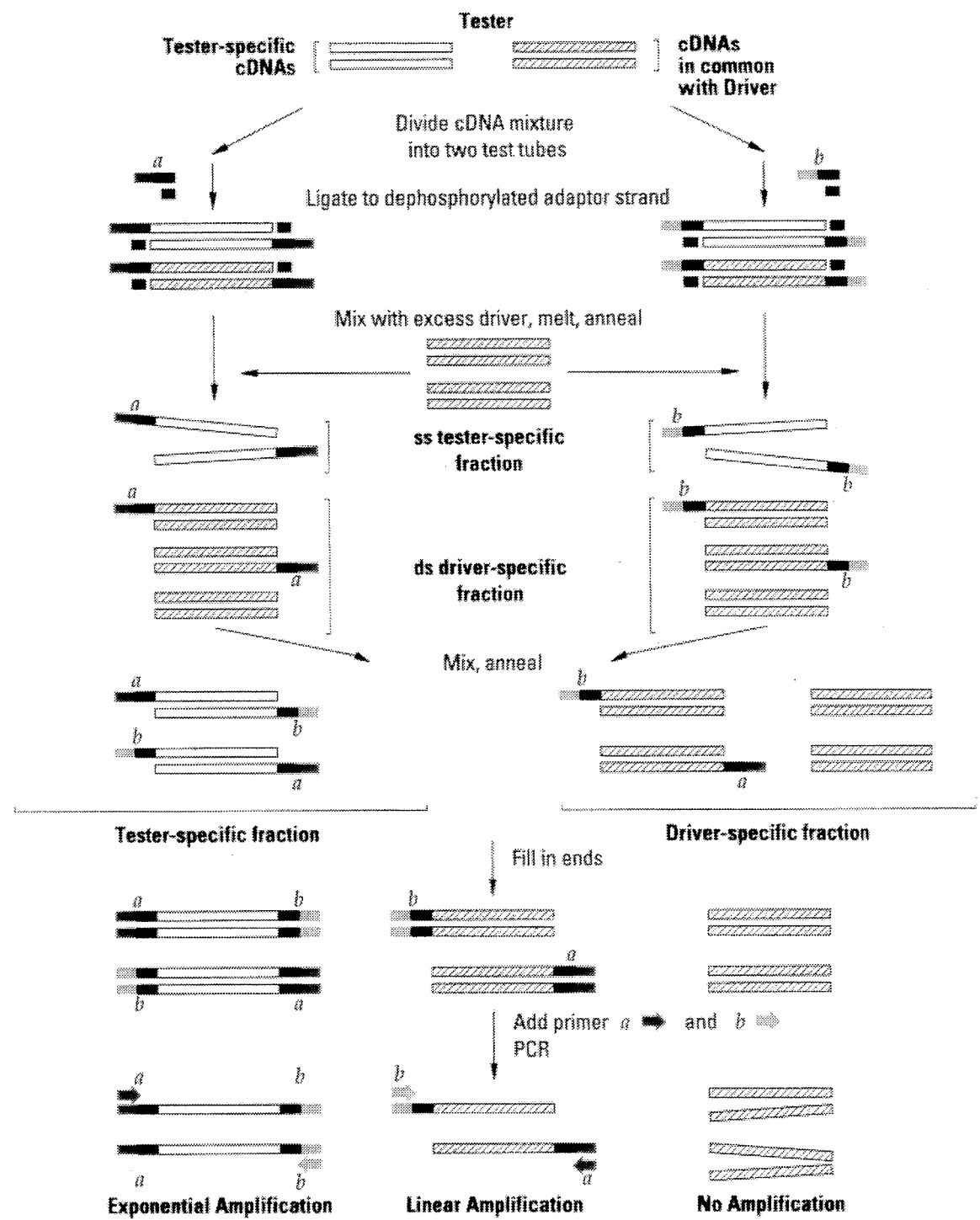
FIG. 4 shows a schematic representation of the preparation of a subtractive cDNA library having a uniform-abundance cDNA population using the subject invention.

In a further aspect, the subject invention can be used in making subtractive cDNA libraries having a uniform-abundance ("equalized") cDNA population. In this embodiment, the subject invention can be used with full-length cDNA libraries, as well as cDNA fragment libraries. Specifically, the subject invention can be used to prepare a cDNA population containing approximately equal representation of all the DNA species that are present in one DNA population (tester), but that are not found in another DNA population (driver). The tester DNA sample is split into two separate samples and the cDNA fragments in each sample are ligated to either adapters a or b in separate test tubes as shown in FIG. 4. After melting and re-annealing in the presence of excess driver cDNA, the single-stranded fraction of tester cDNA fragments is significantly depleted of the more abundant species of cDNAs present in the tester DNA population (this is similar to the equalization mechanism discussed above). At the same time, the single-stranded fraction of the tester DNA population is significantly enriched for any differentially expressed cDNAs (subtraction mechanism) since all common cDNAs which are present in both the tester and driver population will efficiently re-anneal as double-stranded cDNA in the presence of excess driver cDNA. The contents of both test tubes are then mixed and the single-stranded fragments of tester cDNA are additionally re-annealed, equalized and subtracted. The single-stranded ends of the double-stranded DNA fragments can then be filled in.

Primers complementary to the primer binding portion of adapters a and b are added to the tube and PCR performed. Only the self-re-annealed, equalized and subtracted cDNA fraction of tester cDNA fragments have both adapters a and b attached and can be exponentially amplified during PCR. All other DNAs contain either the same adapters at both ends of the DNA fragment (which results in PCR suppression), or only one adapter at one end (which results in linear amplification), or no adapters (i.e., the excess driver DNA). As a result, after PCR amplification, all differentially expressed cDNAs (i.e., those which are unique to the tester DNA population) are simultaneously equalized and enriched relative to the constantly expressed cDNAs. Thus, the subject invention can be used to obtain a highly enriched population of cDNA from low abundance, differentially expressed mRNA.

In another embodiment, the subject invention can be used to subtract a cDNA library (tester) against a set of any cDNAs that have already been cloned into any particular vector (driver). This application of the subject invention is particularly useful for cDNA sequencing projects, such as the human genome sequencing project, where a random strategy to clone all individual cDNAs which are present in a cDNA library has been used. Subtraction of already sequenced cDNAs from a cDNA library should increase the efficiency of identification and sequencing of novel cDNAs which are absent from cDNA databases. Also, the subject invention can be used with subtractive hybridization for identifying differences between tester and driver genomic DNAs. This application of the subject invention is similar to subtractive hybridization of cDNAs, but can be used for discovering probes for pathogenic organisms, for identifying otherwise anonymous loci that have suffered genetic rearrangements, and for detecting the polymorphisms located near the genes affected by inherited disorders.

The subject invention can also be used for the selective amplification (or suppression) of DNA fragments in a defined size range. Because the efficiency of forming suppressive "pan-like" structures is dependent on the DNA fragment length, the subject invention can be used to selectively amplify only those DNA fragments that are longer than a certain length, while at the same time suppressing amplification of DNA fragments that are shorter than the specified length. The size of the smallest DNA fragments which can be amplified depends primarily on differences between the melting temperature of the "pan-like" suppressive structure and the amplification permissive structures. Thus, the size border between the amplified and non-amplified fraction can be optimized to any particular DNA length by varying the length and/or GC content of the suppressor sequence portion of the adapters. Examples of specific adapter sequences and their corresponding primers used for amplifying DNA fragments in a defined size range are shown in Table 2.

TABLE 2

| Adapter/Suppressor/Primer combination | | | | Can amplify DNA fragments longer than |
|---|---|---|---|---|
| ADAPTER Na21-St19 (SEQ ID NO. 1) | PrimerSt19 AGGGCGTGGTGCGGAGGGCxxx 5'-TGTAAGCGTGAAGACGACAGAAAGGGCGTGGTGCGGAGGGCGGT-3' | Suppressor | (SEQ ID NO. 10) | 0.5 kb |

TABLE 2-continued

| Adapter/Suppressor/Primer combination | | | Can amplify DNA fragments longer than |
|---|---|---|---|
| ADAPTER<br>Lu4-St11<br>(SEQ ID NO. 2) | Primer St1<br>ACTCTCCGACCTCTCACCGAGxxxx<br>5'-CGACGTGGACTATCCATGAACGCAACTCTCCGACCTCTCACCGAGCGGT-3' | Suppressor<br>3'-GCCTCCCGCCA-5'<br>3'-GGCTCGCCA-5' | (SEQ ID NO. 11)<br><br>(SEQ ID NO. 12) | 1 kb |
| ADAPTER<br>Na23-St7<br>(SEQ ID NO. 3) | Primer Na23<br>CTCTGGCATCAACTCGGACTAxxxxxxxxxxxxxxxxxxxxx<br>5'-CTCTGGCATCAACTCGGACTATCTCTTCGTCATCTCACCAAG-3' | Suppressor<br><br>3'-AGTAGAGTGGTTC-5' | | 2 kb |
| ADAPTER<br>Lu3-St24<br>(SEQ ID NO. 4) | Primer Lu3<br>AGCACTCTCCAGCCTCTCACCGCAxxxxxxxxxxxxxxxxxxxxxxxxx<br>5'-AGCACTCTCCAGCCTCTCACCGCAATAGCGTGGTCTGCAGGGATGGGT-3' | Suppressor<br><br>3'-CCCTACCCA-5' | (SEQ ID NO. 13) | 3 kb |
| ADAPTER<br>Na21-St19<br>(SEQ ID NO. 1) | Primer Na21<br>TGTAAGCGTGAAGACGACAGAAxxxxxxxxxxxxxxxxxxxxxxxx<br>5'-TGTAAGCGTGAAGACGACAGAAAGGGCGTGGTGCGGAGGGCGGT-3' | Suppressor<br><br>3'-GCCTCCCGCCA-5' | (SEQ ID NO. 14) | 5 kb |
| ADAPTER<br>T7-NotSrf<br>(SEQ ID NO. 5) | Primer T7<br>GGATCCTAATACGACTCACTATAGGGCxxxxxxxxxxxxxxxxxxxxxx<br>5'-CTAATACGACTCACTATAGGGCTCGAGCGGCCGCCCGGGCAGGT-3' | Suppressor<br><br>3'-CCCGTCCA-5' | (SEQ ID NO. 15) | 7 kb |

NOTE:
The "x"s shown in the table do not represent actual nucleotides of the primer; they merely are included to delineate the junction between the primer binding portion and the suppressor of the adapter.

When used in accordance with this embodiment, the subject invention can be used in place of gel filtration exclusion chromatography, a technique which is commonly used to fractionate DNA fragments according to their length. The subject method is also particularly useful for selectively amplifying only full-sized, high molecular weight products using PCR (particularly when used in conjunction with long distance PCR technology), thereby reducing the background in PCR after amplification. The subject invention can also be used to prepare full-sized cDNA (generally, this includes those cDNAs more than 500 bp in length) suitable for cDNA library construction by using adapters which suppress the amplification of cDNAs that are less than about 500 bp in length. The amplification products can then be used directly in cDNA library construction without having to fractionate the cDNA using a gel filtration exclusion chromatography step.

Figure 5:
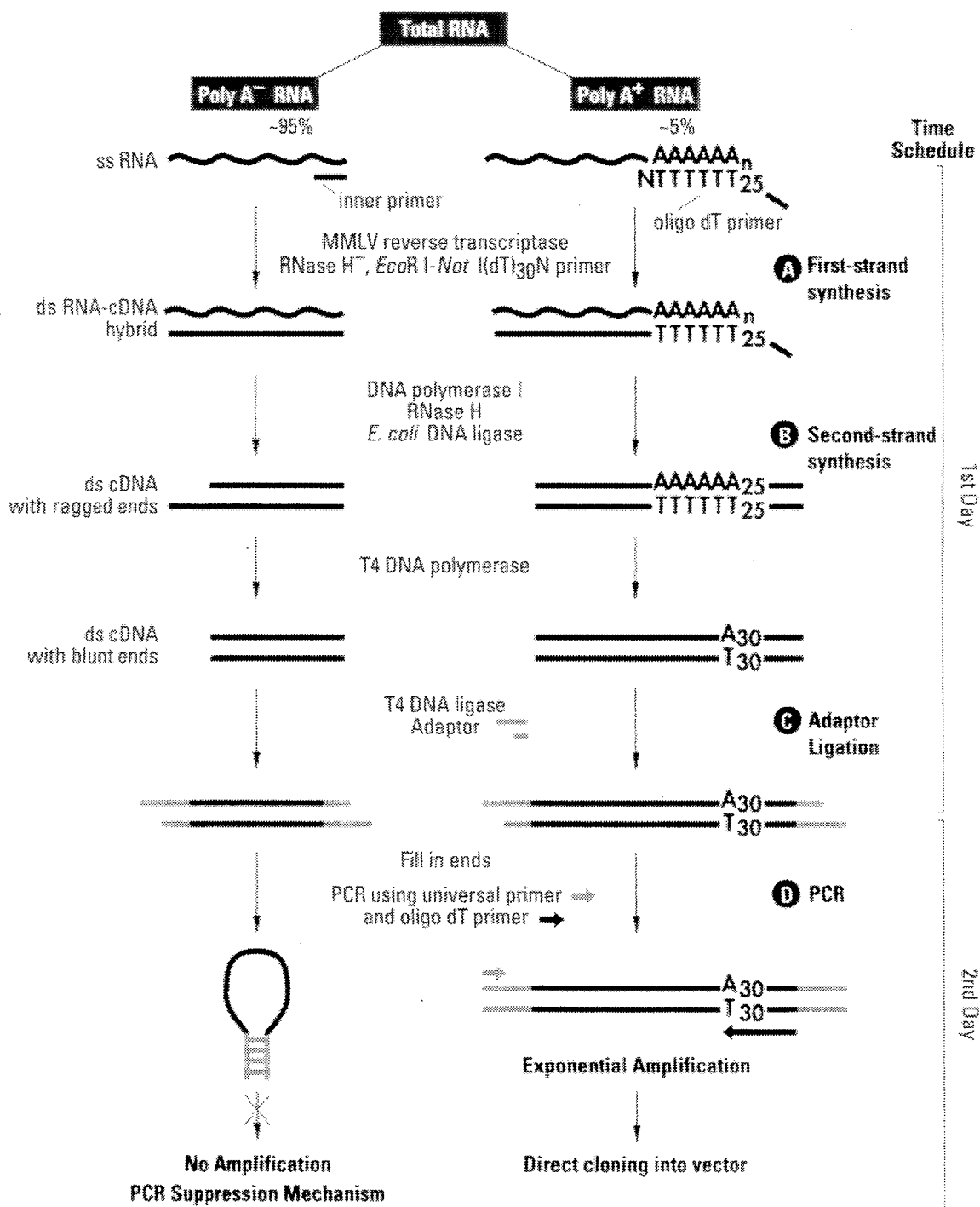
FIG. 5 shows a schematic representation of the preparation of a cDNA library corresponding to poly(A)⁺ RNA from a total RNA template using the subject invention.

In another embodiment, the subject invention can be used for cDNA library construction using total RNA as a starting material. Typically, after the first and second strand cDNA synthesis using total RNA as a template, a large majority of all the cDNA corresponds to the poly(A)$^-$ fraction of the RNA, while only a small fraction corresponds to the poly(A)$^+$ fraction. Moreover, total RNA preparations commonly contain genomic DNA impurities which can also contaminate the cDNA library. In order to selectively amplify the cDNA fraction corresponding only to the poly(A)$^+$ RNA fraction, an adapter of the subject invention is ligated to the entire cDNA population. As shown in FIG. 5, only the cDNA fraction corresponding to poly(A)$^+$ RNA (i.e., the cDNA which contains an internal poly(A) sequence) can be exponentially amplified using an oligo (dT) primer in combination with another PCR primer that is complementary to the primer binding portion of the adapter. All other cDNAs which lack the internal poly(A) sequence (i.e., genomic DNA fragments or those cDNAs reverse transcribed from the poly(A)$^-$ fraction of RNA) are not efficiently amplified because they can form the "pan-like" suppressive structure during PCR amplification.

The subject invention can also be used in conjunction with the procedure for rapid amplification of 5'- and 3'-cDNA ends (RACE) (Belyavsky et al., 1989; Frohman, M. A., et al., 1988). This embodiment of the subject invention allows for the selective amplification of the 5'- or 3'-end of double-stranded cDNA that has an adapter of the subject invention attached at both ends of the cDNA. Using a combination of an internal target DNA primer that is complementary to a portion of the nucleotide sequence of the target DNA, in conjunction with a primer that is complementary to the primer binding portion of the adapter, only the 5'- or 3'-end of any individual RNA is exponentially amplified during the course of the PCR. The non-target cDNAs that lack the internal primer binding sequence that is specific to the target cDNAs are not efficiently amplified because the single strands of the non-target cDNAs can form the suppressive "pan-like" structure.

Optionally, the 5'- and 3'-RACE amplification products can be fused to create a full-length cDNA. The 5'- and 3'-RACE products are purified and then mixed together in the absence of primers. The mixture is subject to several rounds of PCR thermal cycling in the presence of a DNA polymerase. Preferably, the DNA polymerase comprises a combination of thermostable DNA polymerases suitable for long distance (LD) PCR, such as Taq DNA polymerase and Pfu or Vent polymerase. The overlapping regions of the RACE products anneal and are then extended to generate the full-length cDNA. A final LD PCR is performed using the adapter-specific and gene-specific primers and the LD PCR enzyme mixture.

The subject invention can also be used in a large number of applications which require amplification of DNA fragments where a sequence for only a portion of the target DNA is known. The PCR suppression technology of the subject invention provides a novel means for performing this "one-sided" PCR, thereby enabling the skilled artisan to amplify any uncharacterized sequence that is adjacent to a known sequence. "One-sided" PCR using the PCR suppression technology of the subject invention can be used in a variety of applications, including "genomic walking," sequencing of yeast artificial chromosomes insert termini and cosmid insert termini, mapping of introns in genomic DNA from cDNA clones, mapping of regions containing deletions, insertions, etc., and for the sequencing of large clones without having to resort to subcloning.

In one embodiment of this method, genomic DNA is fragmented, preferably using restriction enzymes. Adapters of the subject invention are ligated to both ends of the DNA fragments. Using a combination of a first primer which is complementary to a known sequence on the target DNA and a second primer which is complementary to the primer binding portion of the adapter, the unknown genomic sequence adjacent to the known sequence on the target DNA can be amplified by PCR to produce a product which does not contain the self-annealing complementary sequences at both ends of the DNA fragment. This product can then be exponentially amplified during PCR. The non-target DNA fragments that lack the known sequence complementary to the first primer cannot be efficiently amplified during PCR because the self-annealing complementary sequences attached to the ends of each DNA fragment can form the suppressive "pan-like" structure during PCR. The terminus of the amplified PCR product can then be sequenced and new primers complementary to the sequence prepared. Additional PCR can then be performed on DNA fragments using the new primer and an adapter-specific primer. Repeating the method of the subject invention using the newly discovered primer sequence obtained from each previous PCR amplification product allows the skilled artisan to walk upstream or downstream on the genomic DNA from the point of initiation.

Following are examples which illustrate procedures, including the best mode, for practicing the invention. These examples should not be construed as limiting. As would be readily apparent to a person skilled in the art, the subject invention can be applied to a variety of molecular biology techniques and procedures other than those specifically exemplified herein. All percentages are by weight and all solvent mixture proportions are by volume unless otherwise noted.

Example 1—Rapid Amplification of 5'- and 3'-Ends of cDNA (RACE)

The PCR suppression technology of the subject invention has been used to amplify the 5'- and 3'-ends of a variety of different individual cDNAs. Specifically, the procedure and results of a PCR RACE of human transferrin receptor cDNA and human beta-actin cDNA using human placenta poly (A)$^+$ RNA or human placenta total RNA as a starting material are described herein. The human transferrin receptor mRNA is a relatively rare transcript in placental RNA, whereas beta-actin mRNA is relatively abundant.

Figure 6:
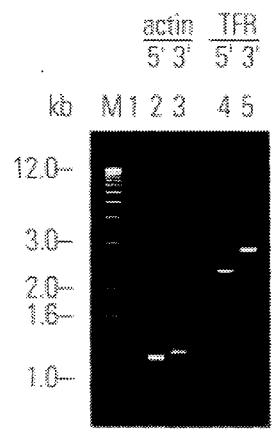
FIG. 6 shows the PCR amplification products after 5'- and 3'-RACE of human β-actin cDNA (lanes 2, 3) and human transferring receptor cDNA (lanes 4, 5) resolved on a 1.2% agarose/ethidium bromide gel. Human placenta double-stranded cDNA ligated with the T7-NotSrf adapter was used as a template. Lanes 2 and 4 show 5'-RACE products, whereas lanes 3 and 5 show the 3'-RACE products. Lane 1 is a negative control (i.e., PCR amplification using only one 5'/3'-universal primer). Lane M contains 1 Kb DNA size marker.

Human double-stranded cDNA obtained after first and second strand cDNA synthesis using RNA as a template was ligated with the T7-NotSrf adapter (SEQ ID NO. 5). FIG. 6 shows the results of 5'- and 3'-RACE for the human beta-actin gene and the transferrin receptor gene using a combination of a gene-specific primer and the T7 primer (SEQ ID NO. 15) of the subject invention. After PCR using the subject invention, the observed RACE product size was in accordance with the expected size given the inner gene specific primer (human beta-actin: 5'-RACE product—1.2 kb, 3'-RACE product—0.8 kb; human transferfin receptor: 5'-RACE product—2.3 kb, 3'-RACE product—2.8 kb). The identity of the RACE PCR products corresponding to the transferfin and beta-actin genes were confirmed by restriction enzyme digestion and sequence analysis of the PCR products. The specific RACE experimental procedure is described below.

PROTOCOL A: First-strand cDNA synthesis

This reaction is designed to convert 1 µg of Poly (A)$^+$ RNA into first-strand cDNA. The same protocol can be applied using 1 µg of total RNA.

1. Combine the following in a sterile 0.5 ml microcentrifuge tube:

| | |
|---|---|
| Human placenta poly (A)$^+$ RNA (in 1–4 µl) | 1 µg |
| RI-Not-T30 primer (10 µM) (SEQ ID NO. 20) | 1 µl |

Add sterile H$_2$O to a final volume of 5 µl. Mix contents and spin the tube briefly in a microcentrifuge.

2. Incubate the tube in a 70° C. water bath for 3 minutes or use a thermocycler for the same purpose.

3. Cool the tube on ice for 2 minutes. Spin down the contents of the tube briefly in a microcentfifuge.

4. Add the following to the same reaction tube:

| | |
|---|---|
| 5X First-strand buffer | 2 µl |
| (250 mM Tris-HCl, pH 8.3, 30 mM MgCl$_2$, 375 mM KCl) | |
| dNTP mix (10 µM each dATP, dTTP, dCTP, dGTP) | 1 µl |
| MMLV Reverse Transcriptase (ribonuclease H free) (200 units/µl) | 1 µl |

5. Mix the contents of the tube by gently vortexing and spin the tube briefly.

6. Incubate the tube at 42° C. for 1 hour in an incubator or thermocycler.

7. Place the tube on ice to terminate first-strand synthesis and proceed to protocol B.

PROTOCOL B: Second-Strand Synthesis

The protocol is suitable for synthesizing second-strand cDNA from the first-strand cDNA prepared in the first-strand reaction (Protocol A).

1. Add the following components previously cooled on ice to the reaction tube from Protocol A:

| | |
|---|---|
| Sterile H$_2$O | 48.4 µl |
| 5X Second-strand buffer | 16 µl |
| (500 mM KCl, 50 mM ammonium sulfate, 25 mM MgCl$_2$, 0.75 mM NAD, 100 mM Tris-HCl (pH 7.5), 0.25 µg/ml BSA) | |
| 4 dNTP mix (10 mM each dATP, dTTP, dCTP, dGTP) | 1.6 µl |
| 20X Mixture of E. coli DNA polymerase I, E. coli DNA Ligase, RNase H (6 units/µl, 1.2 units/µl, 0.25 units/µl) | 4 µl |

2. Mix contents and spin the tube briefly. The final volume should be about 80 µl.

3. Incubate the tube at 16° C. (water bath or thermocycler) for 2 hours.

4. Add 1 µl (5 units) of T4 DNA polymerase, mix the contents well, and incubate the tube at 16° C. for 30 minutes in a water bath or thermocycler.

5. Add 4 µl of 0.2M EDTA to terminate second-strand synthesis.

6. Add 100 µl of phenol:chloroform:isoamyl alcohol (25:24:1).

7. Vortex thoroughly, and spin the tube in an Eppendorf microcentrifuge at 14,000 rpm for 10 minutes to separate the phases.

8. Remove the top aqueous layer and place this layer in a clean 0.5 ml microcentrifuge tube. Discard the interphase and lower phase.

9. Add 100 µl of chloroform:isoamyl alcohol (24:1) to the aqueous layer.

10. Repeat steps 7 and 8.

11. Add a ½ volume (about 30 µl) of a 4M ammonium acetate solution and 2.5 volumes (of the total resulting volume in the tube) of 95% ethanol to the reaction. Vortex the mixture thoroughly and spin the tube immediately in a Eppendoff microcentrffuge at 14,000 rpm for 20 minutes.

12. Remove the supernatant carefully and overlay the pellet with 300 µl of 80% ethanol. Centrifuge in an Eppendorf centrffuge for 10 minutes at 14,000 rpm and remove the supernatant.

13. Air dry the pellet for 10 minutes to evaporate residual ethanol. Dissolve the precipitate in 10 µl of TE buffer.

PROTOCOL C: Adapter Ligation to DNA

This protocol is suitable for DNA ligation experiments using 5 µl of double-stranded cDNA obtained after second-strand synthesis (Protocol B).

1. Mix the following reagents in 0.5 ml microcentrifuge test tube in the order shown:

| | |
|---|---|
| ds cDNA | 5 µl |
| T7 NotSfr Adapter (10 µM) (SEQ ID NO. 5) | 2 µl |
| 5X DNA ligation buffer (250 mM Tris HCl, pH 7.8, 50 mM MgCl₂, 10 mM DTT, 25% PEG 8000, 5 mM ATP) | 2 µl |
| T4 DNA ligase (1 unit/µl) | 1 µl |

2. Vortex and spin briefly in an Eppendorf microcentrifuge.

3. Incubate the tube at 16° C. overnight.

4. Heat the tube at 70° C. for 5 minutes to inactivate the T4 ligase.

5. Dilute 1 µl of the reaction mixture with 250 µl of TrE buffer (20 mM Tricine-KOH, pH 9.5, EDTA 0.2 mM). Heat at 96° C. for 2 minutes, then cool on ice.

PROTOCOL D: 5'- and 3'-RACE

1. Prepare enough PCR reaction mix for all PCR reactions. For one PCR reaction (50 µl total volume) mix the following reagents:

| | |
|---|---|
| 10X PCR Buffer (200 mM TrisHCl, pH 8.55, 160 mM ammonium sulfate, 25 mM MgCl₂, 1.5 mg/ml BSA) | 5 µl |
| H₂O | 35 µl |
| 4 dNTP (10 mM each dATP, dTTP, dCTP, dGTP) | 1 µl |
| 25X KlenTaq/Pfu DNA Polymerase/anti-DNA polymerase antibody ("TaqSTART Antibody", CLONTECH, Palo Alto, CA) mixture (6,000 units/ml, 37 units/ml, 0.8 mg/ml) | 2 µl |

Final volume should be 43 µl. The same PCR reaction mixture can be used for both 5'- and 3'-RACE protocols. Mix well by vortexing, then briefly spin the tube in a microcentrifuge.

2. Mix the components in 0.5 ml PCR test tubes (Perkin-Elmer GeneAmp 0.5 ml reaction tubes), in the order shown, according Table 3.

TABLE 3

| | Test Tube No. | | |
|---|---|---|---|
| | 1 | 2 | 3 |
| Description | Negative Control | 5'-RACE | 3'-RACE |
| Adapter Ligated cDNA | 5 µl | 5 µl | 5 µl |
| T7 Primer (10 µM) (SEQ ID NO. 15) | 1 µl | 1 µl | 1 µl |
| 5'-RACE gene specific inner primer (10 µM)* | — | 1 µl | — |
| 3'-RACE gene specific inner primer (10 µM)* | — | — | 1 µl |
| H₂O | 1 µl | — | — |
| PCR reaction mix | 43 µl | 43 µl | 43 µl |
| Final volume | 50 µl | 50 µl | 50 µl |

*For human beta actin cDNA the sequences of the primers:
5'-RACE primer: 5':ACTCGTCATACTCCTGCTTGCTGATCCA-CATCTGC-3' (SEQ ID NO. 23)
3'-RACE primer: 5':ACCTGACTGACTACCTCATGAAGATCCTCA-3' (SEQ ID NO. 24)
For human transferrin receptor cDNA:
5'-RACE primer: 5':GTCAATGTCCCAAACGTCACCAGAGA-3' (SEQ ID NO. 25)
3'-RACE primer: 5':CTGCCAGCTTTACTGGAGAACTTGA-3' (SEQ ID NO. 26)
Note:
Tubes 2 and 3 are used to amplify the 5'- and 3'-end of the β-actin cDNA, and tubes 4 and 5 are used for amplifying the transferrin receptor cDNA.

3. Overlay each test tube with 2 drops of mineral oil and run in thermocycler using the following program: 94° C. for 1 minute, followed by 28 cycles at (90° C. for 30 seconds, then 68° C. for 5 minutes)

4. Remove 5 µl from each test tube and subject them to 1.2% agarose gel electrophoresis. For comparison purposes, a 1 kb DNA size marker (Gibco-BRL) was also run on the gel.

Example 2—Genomic Walking

The subject invention was also used to perform a "genomic walk" upstream from exon 2 at the 5'-end of a human tissue plasminogen activator (TPA) gene sequence to the promoter region of this gene using genomic DNA and a combination of primers complementary to adapters of the subject invention and primers specific to the TPA gene. "Genomic walking" is a technique whereby overlapping DNA fragments are sequentially isolated in order to "walk" up or down a larger polynucleotide segment, such as a chromosome.

Human genomic DNA (4 µg) (CLONTECH, Palo Alto, Calif.) was digested overnight at 37° C. in separate test tubes with 80 units of each of the following restriction enzymes: EcoRV, ScaI, PvuII, SspI or DraI using the buffer recommended by the supplier (Gibco-BRL). The DNA was extracted once with phenol/chloroform/isoamylalcohol (25/24/1) and precipitated by addition of ⅒th volume 3M NaOAc, 20 µg of glycogen and two volumes of 95% ethanol. The tubes were vortexed and immediately centrifuged at 14000 g in a microcentrifuge for 10 minutes. The pellets were washed with 80% ethanol and immediately centrifuged as above for 5 minutes, air dried and then dissolved in 20 µl of 10 mM Tris-HCl, pH 7.5, 0.1 mM EDTA (TE buffer). 10 µl of DNA was then ligated to an excess of adapter T7-NotSrfA (SEQ ID NO. 6) overnight at 16° C. using the following: 50mM TrisHCl, pH 7.6, 10 mM MgCl₂, 0.5 mM ATP, 10 mM DTT, 5 µM adapter T7-NotSrfA and 1 unit of T4 DNA-ligase (Gibco-BRL). The ligation reaction was terminated by incubation of the tubes at 70° C. for 5 minutes, and diluted 10-fold by addition of 180 µl of TE buffer.

A primary PCR reaction was conducted utilizing a thermostable DNA polymerase mixture comprising Tth polymerase (Toyobo) and Vent polymerase (New England BioLabs) at ratio of 20:1 (vol/vol). This results in a unit ratio of 50:1. A commercially available enzyme mixture of Tth XL (Perkin Elmer) was also used with similar results. Before use, 1 µl (5.5 µg) of "TthSTART" antibody (anti-Tth polymerase antibodies, CLONTECH) was mixed with 10 µl of the Tth/Vent enzyme mixture.

PCR reactions were conducted in 50 µl volumes containing 1 µl of ligated DNA, 40 mM Tris-HCl, pH 9.3, 85 mM KOAc, 1.1 mM MgOAc, 0.4 µM of the primers T7 (SEQ ID NO. 15) and TPA 1 (SEQ ID NO. 21) and 0.8 µl of the Tth/Vent enzyme/"TthSTART" antibody mixture. Cycle parameters were as follows: denaturation at 94° C. for 30 seconds and annealing/extension at 68° C. for 6 minutes except that the first denaturation step was for 1 minute and the final annealing/extension time was lengthened to 13 minutes. Thirty (30) cycles of primary PCR were typically used.

A secondary PCR reaction was conducted with 1 µl of a 100-fold dilution of the primary PCR product using the same reaction components and parameters as for the primary PCR except that primers NotSff 4 (SEQ ID NO. 18) and TPA2 (SEQ ID NO. 22), 0.4 µl of the Tth/Vent enzyme/"TthSTART" antibody mixture and 20 cycles were used. PCR products were examined on a 1.2% agarose/ethidium bromide (EtBr) gel. For restriction enzyme digestion of PCR products, 10 µl of corresponding PCR products were mixed with 1.2 µl of 10× concentrated enzyme buffer, and 10 units of restriction enzyme (Gibco-BRL) and incubated at 37° C. for 4 hours.

Figure 7:
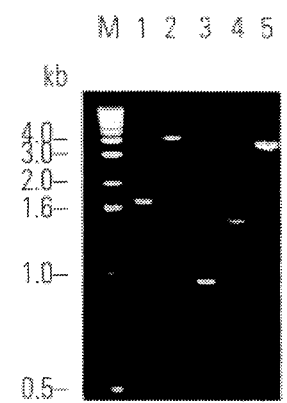
FIG. 7 shows "one-sided" PCR amplification products that were resolved on a 1.2% agarose/ethidium bromide gel. The amplification products were generated by "walking" upstream from exon 2 of the human TPA gene using the subject invention. PCR products in lanes 1–5 were obtained from human genomic DNA digested with: EcoRV (lane 1), ScaI (lane 2), DraI (lane 3), PvuII (lane 4) or SspI (lane 5). The outside lanes (M) show a 1 kb DNA size marker.

FIG. 7 shows that for each restriction digest essentially a single band corresponding in length to the distance between the gene-specific primer and the particular restriction site in the promoter region of the TPA gene was identified after gel electrophoresis. The identity of the amplified products were also confirmed by restriction enzyme analysis.

Example 3—Selective Amplification of DNA Fragments in a Defined Size Range

The PCR suppression technology of the subject invention was also used to selectively amplify cDNA fragments within a defined size range. Specifically, amplification of DNA fragments shorter than a certain length was selectively suppressed, while longer DNA fragments were efficiently amplified. Several sets of adapters which give efficient amplification of target DNA in different size ranges were developed. These include adapters that only allow amplification of fragments longer than 500 bp, longer than 1 kb, longer than 2 kb, longer than 3 kb, longer than 5 kb, and longer than 7 kb. Examples of these size-dependent adapters are shown in Table 2.

In one embodiment of the subject invention, the Na21-St19 adapter (SEQ ID NO. 1) was used to selectively amplify DNA fragments that were more than 5 kb in length. Specifically, double-stranded cDNA was prepared from human skeletal muscle and ligated with adapter Na21-St19 as described in Example 1. The same PCR amplification protocol set forth in Example 1 (but without the gene-specific primers) was used, except that in one PCR reaction the Na21 primer (SEQ ID NO. 14) was used to amplify the cDNA in a defined size range. In a separate PCR reaction, the St19 primer (SEQ ID NO. 10) (which is complementary to the suppressor sequence on the adapter) was used as a positive control to amplify the entire cDNA population. The following amplification program was used: 94° C. for 1 minute, followed by 15–19 cycles at (90° C. for 30 seconds, then 68° C. for 5 minutes). The amplification products were then run on an agarose gel.

Figure 8:
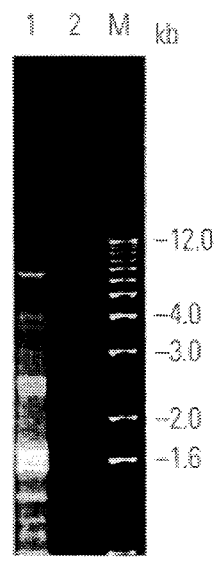
FIG. 8 shows the 6.5 kb myosin cDNA PCR product obtained after size selective amplification of human skeletal muscle double-stranded cDNA ligated with adapter Na21-St19. Lane 1: 15 cycles of PCR using inner primer St19. Lane 2: 19 cycles of PCR using outer primer Na21. Lane M: DNA size markers.

The PCR amplification products from each reaction are shown in FIG. 8. Human skeletal muscle poly (A)$^+$ RNA contains several highly abundant individual RNAs which give corresponding bright DNA bands in the size range of 0.1 to 6.5 kb after PCR using the St19 primer (i.e., PCR without the size suppression effect, lane 1). However, when the Na21 primer is used in the PCR reaction, only selective amplification of the 6.5 kb band, which corresponds to myosin cDNA, was detected (lane 2). All other cDNAs having a length less than 5 kb were not amplified under these conditions.

Example 4—cDNA Library Construction From Total RNA

A serious problem in the construction of cDNA libraries from total RNA is the very high level of amplification of DNA fragments that correspond to cDNA that is reverse transcribed from the poly (A)$^-$ RNA fraction or genomic DNA impurities. The PCR suppression technology of the subject invention was used to selectively suppress amplification of the cDNA fraction corresponding to the poly(A)$^-$ RNA or genomic DNA. Human skeletal muscle cDNA was prepared and T7-NotSrf adapter (SEQ ID NO. 5) was ligated to a whole cDNA population as described in Example 1. PCR amplification was then performed as described in Example 1, except that the RI-Not-T30 primer (SEQ ID NO. 20) (which is complementary to the internal poly A sequence of all poly (A)$^+$ RNAs) was used in combination with the outer suppressor-specific primer T7 (SEQ ID NO. 15). cDNAs which do not possess internal poly(A) sequences cannot be efficiently amplified because they form the "pan-like" suppressor structure during the PCR reaction.

Figure 9:
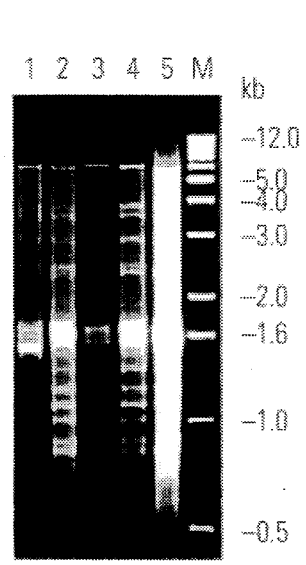
FIG. 9 shows the PCR products amplified using a template of ds cDNA ligated with adapter T7-NotSrf. double-stranded cDNA was synthesized from either human skeletal muscle poly(A)⁺ RNA (lanes 1, 2) or total RNA (lanes 3–5). Lanes 1, 4, and 5: 19 cycles of PCR. Lanes 2 and 3: 15 cycles of PCR. Lane M contains DNA size markers.

FIG. 9 shows that the banding pattern of PCR products obtained from total RNA (lane 3, 4) amplified as described above is very similar to the pattern obtained using cDNA reverse transcribed from poly (A)$^+$ RNA (lane 1, 2). As a control, standard adapter Ad1SGT (SEQ ID NO. 7), which lacks a suppressor sequence portion, was ligated to cDNA obtained from total RNA. The PCR primer Na1SGT (SEQ ID NO. 16), which corresponds to the upper strand of the Ad1SGT adapter, was added and the mixture subjected to PCR (The results are shown in lane 5). In the absence of the suppression effect of the subject invention, the banding pattern of PCR products amplified from cDNA derived from total RNA does not correspond to the pattern of PCR products amplified from cDNA reverse transcribed from poly (A)$^+$ RNA.

Example 5—Generation of Subtracted cDNA

The PCR suppression technology of the subject invention has also been used with a subtractive hybridization protocol. Double-stranded cDNA prepared from human skeletal muscle and digested with Rsa I restriction endonuclease was used as the driver DNA. A mixture of human skeletal muscle cDNA combined at different ratios with Rsa I digested phiX174 plasmid DNA (CLONTECH) was used as the tester DNA.

Human skeletal muscle cDNA was prepared as described in Example 1, Protocol B. The double-stranded cDNA was subdivided into two test tubes (tester DNA and driver DNA test tubes). Either 0.1% or 0.01% of phiX174 DNA was added to the tester DNA test tube and the cDNA fractions in both tubes were digested using 10 units of Rsa I restriction endonuclease per 1 μg of DNA for 2 hours at 37° C. in a buffer containing 10 mM Bis Tris Propane-HCl, 10 mM MgCl₂, and 1 mM dithiothreitol, pH 7.0. After a phenol/chloroform extraction and ethanol precipitation, adapters T7-NotSrf (SEQ ID NO. 5) and Na21-St19 (SEQ ID NO. 1) were ligated to the tester DNA (0.3 μg) in separate test tubes (A and B, corresponding to DNA ligated with adapter T7-NotSrf and adapter Na21-St19, respectively) as described in Example 1, Protocol C.

For subtractive hybridization, 0.3 μg of tester DNA and 4.5 μg of driver cDNA were mixed (in both tube A and B), ethanol-precipitated, dissolved in 3 μl of HB buffer (50 mM HEPES-KOH, pH 8.3, 0.5M NaCl, 0.2 mM EDTA, 10% Polyethylene glycol (8,000)), overlaid with 25 μl of mineral oil (Perkin-Elmer Cetus), denatured at 94° C. for 2 minutes and hybridized for 10 hours at 68° C. Next, the contents of both tubes A and B were mixed together, then 5 μg of freshly heat denatured (94° C. for 2 minutes) driver DNA in 1 μl of HB buffer was added and hybridized for an additional 10 hours at 68° C. At the end of the hybridization, the resulting cDNA was diluted in 120 μl of HSE buffer (10 mM HEPES-KOH, pH 8.3, 50 mM KCl, 0.2 mM EDTA), heated at 72° C. for 10 minutes and amplified as described in Example 1, Protocol D (but without the gene-specific primers) using PCR primers T7 and Na21, except that the following PCR program was used: 75° C. for 5 minutes, then 94° C. for 1 minute, followed by 25 cycles at (90° C. for 30 seconds, then 68° C. for 5 minutes). The first PCR program step (75° C. for 5 minutes) is required to fill in ends of the re-annealed tester DNA before PCR cycles. After the first round of PCR, the PCR mixture was diluted 100-fold in HSE buffer and subjected to a second round of "nested" PCR. This round of PCR was carried out as described for the first round of PCR but using the following nested PCR primers:

St19 (SEQ ID NO. 10): 5'-AGGGCGTGGTGCG-GAGGGC-3'

NotSrf1 (SEQ ID NO. 17): 5'-TCGAGCGGCCGC-CCGGGCAGGT-3'

Final PCR products were analyzed on a 6% acrylamide—7M urea gel or a 2% agarose gel.

Figure 10:
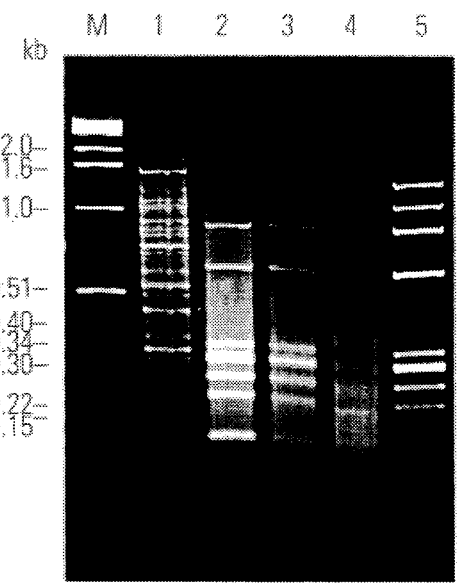
FIG. 10 shows the PCR enrichment of plasmid DNA after subtractive hybridization. Lane 1: skeletal muscle cDNA fragments mixed with 0.1% plasmid DNA (PhiX174) digested by Rsa I before subtraction. Lane 2: The same as in lane 1 but after subtraction. Lane 3: The same as in lane 2, but using 0.01% of plasmid DNA initially digested by Rsa I. Lane 4: skeletal muscle cDNA digested by RsaI (without plasmid DNA) after substraction. Lane 5: plasmid DNA (PhiX174) digested by RsaI. Lane M contains 1 kb DNA size marker.

FIG. 10 shows the efficiency of enrichment of plasmid DNA in the tester cDNA after one round of subtractive hybridization using 25-fold overall excess of driver cDNA, followed by amplification of the subtracted cDNA. Subtractive hybridization enrichment of tester cDNA containing 0.1% (lane 2) or 0.01% (lane 3) of plasmid DNA by driver cDNA gave bands that corresponded primarily to pure plasmid DNA (shown in lane 5) (each band corresponds to about 0,002% abundance of total cDNA); the bands corresponding to human skeletal muscle cDNA (lane 1 and lane 4) were eliminated. These results show that after one round of subtractive hybridization using the PCR suppression technology of the subject invention at least a several hundred-fold enrichment of rare DNA sequences that are present in the tester but absent in the driver DNA population (i.e., those sequences comprising 0.002% or less of the total messenger population) can be achieved.

Example 6—Selective Recovery of Common Sequences Shared by Two Complex and Partially Coincident cDNA Mixtures PCR Suppression technology of the subject invention was used to construct a cDNA library that is enriched for those cDNA sequences that are conserved between human (HeLa) and hamster (Chinese hamster fibroblasts) cell lines. First-strand cDNA was synthesized from HeLa poly (A)⁺ RNA using the Lu3-T13 primer (SEQ ID NO. 8). First-strand cDNA was prepared from hamster fibroblast poly (A)⁺ RNA using the Lu4-T13 primer (SEQ ID NO. 9). The cDNAs were prepared in separate test tubes. Oligo (dA) terminal tailing of the first-strand cDNA by terminal transferase, followed by amplification of the cDNA using either primer Lu3-T13 or Lu4-T13 was carried out essentially as previously described (Belyavsky et al. 1989). PCR cDNA products from each test tube were treated with exonuclease III under conditions of partial digestion and then mixed, hybridized and amplified using a combination of the Lu3 (SEQ ID NO. 13) and Lu4 (SEQ ID NO. 19) primers (Lisitsyn et al., 1993). The final conserved (between human and hamster) PCR cDNA products were cloned into a "pBLUESCRIPT II" (KS+) vector (Stratagene, LaJolla, Calif.).

Plasmid DNA from 25 random clones was purified and then hybridized (in dot-blot format) with poly(A)⁺ RNA purified from human HeLa and hamster fibroblast cells. All 25 cDNA clones showed a hybridization signal of similar intensity with both poly(A)⁺ RNAs, even under very stringent hybridization conditions (hybridization—2×SSC, 68° C.; washing stage—0.1×SSC, 70° C.). Inserts from the five clones which gave the biggest differences in hybridization signal for the human and hamster poly(A)⁺ RNA have been sequenced and analyzed for homology in a DNA sequence database (EMBL Data Library) using the GCG FASTA program (University of Wisconsin). Two clones corresponded to the sequence of human H3.3 histone cDNA, a gene which is more than 96% conserved in DNA sequence among all mammalian species examined thus far (Wells et at, 1987). One clone contained the sequence of a poly(A)-binding protein, which is also highly conserved in mammals (90% homology). The DNA sequence of the final two clone inserts did not correspond to any homologous sequence in the DNA database; however, PCR primers synthesized using the sequence of these two clones produced identical size PCR products using human and hamster genomic DNA as a template. Thus, the cDNA library obtained using the PCR suppression technology according to the subject invention contained at least 96% of the cDNA clones that were conserved between human and hamster DNA at the nucleotide sequence level.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Barnes, W. M. (1994) "PCR amplification of up to 35-kb DNA with high fidelity and high yield from λ bacteriophage templates," *Proc. Natl. Acad. Sci. USA* 91:2216–2220.

Belyavsky, A., et al. (1989) "PCR-based cDNA library construction: general cDNA libraries at the level of a few cells," *Nucl. Acids Res* 17:2919–2932.

Brookes, A. J., and D. J. Porteous (1991) "Coincident sequence cloning," *Nucl. Acids Res.* 19:2609–2613.

Cheng, S., C. Fockler, W. M. Barnes, and R. Higuchi (1994) "Effective amplification of long targets from cloned inserts and human genomic DNA," *Proc. Natl. Acad. Sci. USA* 91:5695–5699.

Frohman, Michael A., Michael K. Dush, and Gail R. Martin (1988) "Rapid production of full-length cDNAs from rare transcripts: Amplification using a single gene-specific oligonucleotide primer," *Proc. Natl. Acad. Sci. USA* 85:8998–9002.

Hampson, I. N., et al. (1992) "Chemical cross linking subtraction (CCLS): a new method for the generation of subtractive hybridization probes," *Nucl. Acids Res.* 20:2899.

Hara, E., et al. (1993) "DNA-DNA subtractive cDNA cloning using oligo $(dT)_{30}$-latex and PCR: Identification of cellular genes which are overexpressed in senescent human diploid fibroblasts," *Anal. Biochem.* 214:58–64.

Jones, Douglas H., and Stanley C. Winistorfer (1993) "Genome walking with 2- to 4-kb steps using panhandle PCR," in PCR methods and applications (CSHL Press) 197–203.

Ko, Minoru S. H. (1990) "An 'equalized cDNA library' by reassociation of short double-stranded cDNAs," *Nucl. Acids Res.* 18:5705–5711.

Kellogg, D. E., I. Rybalkin, S. Chen, N. Mukhamedova, T. Vlasik, P. D. Siebert, and A. Chenchik (1994) "TaqStart Antibody™: "Hot Start" PCR Facilitated by a Neutralizing Monoclonal Antibody Directed Against Taq DNA Polymerase," *BioTechniques* 16(6):1134–1137.

Lisitsyn, Nikolai, Natalya Lisitsyn, and Michael Wigler (1993) "Cloning the differences between two complex genomes," *Science* 259:946–951.

Lukyanov, S. A., N. G. Gurskaya, K. A. Lukyanov, V. S. Tarabykin, and E. D. Sverdlov (1994) "Highly efficient subtractive hybridization of cDNA," *Bioorganic Chemistry* (Russia) 20:701–704.

Mullis, Kary B., Henry A. Erlich, Norman Arnheim, Glenn T. Horn, Randall K. Saiki, Stephen J. Scharf, U.S. Pat. No. 4,683,195, issued Jul. 28, 1987.

Mullis, K. B., U.S. Pat. No. 4,683,202, issued Jul. 28, 1987.

Mullis, Kary B., Henry A. Erlich, Norman Arnheim, Glenn T. Horn, Randall K. Saiki, Stephen J. Scharf, U.S. Pat. No. 4,800,159, issued Jan. 24, 1989.

Riley, J., R. Butler, D. Ogilvie, R. Finnlear, D. Jenner, S. Powell, R. Anand, J. C. Smith, and A. F. Markham (1990) "A novel, rapid method for the isolation of terminal sequences from yeast artificial chromosome (YAC) clones," *Nucl. Acids Res.* 18:2887–2890.

Saiki, Randall K., Stephen Scharf, Fred Faloona, Kary B. Mullis, Glenn T. Horn, Henry A. Erlich, Norman Arnheim (1985) "Enzymatic Amplification of β-Globin Genomic Sequences and Restriction Site Analysis for Diagnosis of Sickle Cell Anemia," *Science* 230:1350–1354.

Sverdlov, E., et al. (1993) "Subtractive hybridization, theoretical analysis and a principle of the 'trapper'," *Bioorganic Chemistry* (Russia) 19:1081–1088.

Timblin, Cynthia, James Battey, and W. Michael Kuehl (1990) "Application for PCR technology to subtractive cDNA cloning: identification of genes expressed specifically in murine plasmacytoma cells," *Nucl. Acids Res.* 18:1587–1593.

Wang, Zhou, and Brown, Donald D. (1991) "A gene expression screen," *Proc. Natl. Acad. Sci.* 88:11505–11509.

Wells, D., et al. (1987) "Unusual structure, evolutionary conservation of non-coding sequences and numerous psevdogenes characterize the human H3.3 histone multigene family," *Nucl. Acids Res.* 15:2871–2889.

---

We claim:

1. A method for selectively suppressing the amplification of a non-target nucleic acid fragment, comprising the steps of:
    (a) attaching a PCR suppression adapter to each end of a nucleic acid fragment;
    (b) contacting said nucleic acid fragment having said attached adapters with a nucleic acid primer comprising a nucleotide sequence that is complementary to a nucleotide sequence of said adapter;
    (c) adding to said mixture obtained after step (b) an effective amount of reagents necessary for performing a PCR; and
    (d) cycling the mixture obtained after step (c) through at least one cycle of the denaturing, annealing and primer extension steps of PCR to obtain an amplification product, wherein amplification of said non-target nucleic acid fragment is suppressed during PCR.

2. The method, according to claim 1, wherein said adapter comprises a primer binding sequence portion and a suppressor sequence portion.

3. The method, according to claim 1, wherein said adapter is selected from the group consisting of Na21-St19 (SEQ ID NO. 1), Lu4-St11 (SEQ ID NO. 2), Na23-St7 (SEQ ID NO. 3), Lu3-St24 (SEQ ID NO. 4), T7-NotSrf (SEQ ID NO. 5), T7-NotSrfA (SEQ ID NO. 6) and Ad1SGT (SEQ ID NO. 7).

4. The method, according to claim 1, wherein said primer is selected from the group consisting of St19 (SEQ ID NO. 10), St1 (SEQ ID NO. 11), Na23 (SEQ ID NO. 12), Lu3 (SEQ ID NO. 13), Na21 (SEQ ID NO. 14), T7 (SEQ ID NO. 15), Na1SGT (SEQ ID NO. 16), NotSrf1 (SEQ ID NO. 17), NotSrf4 (SEQ ID NO. 18), Lu4 (SEQ ID NO. 19), Lu3-T13 (SEQ ID NO. 8), Lu4-T13 (SEQ ID NO. 9), and RI-Not-T 30 (SEQ ID NO. 20).

5. The method, according to claim 1, wherein step (b) comprises contacting said nucleic acid fragment with a first primer comprising a nucleotide sequence that is complementary to a nucleotide sequence of said adapter, and wherein step (b) further comprises contacting said nucleic acid fragment with a second nucleic acid primer comprising a nucleotide sequence that is complementary to a nucleotide sequence of said target nucleic acid fragment to yield an amplification product having one terminus with a nucleotide sequence complementary to said first primer and a second terminus with a nucleotide sequence complementary to said second primer.

6. The method, according to claim 1, wherein said nucleic acid fragment is obtained by digesting a nucleic acid with a restriction endonuclease.

7. The method, according to claim 1, wherein the PCR cycling of step (d) is repeated at least 5 times.

8. The method, according to claim 1, wherein step (b) further comprises adding an antibody that reversibly binds to and inhibits activity of a polymerase in a temperature-specific manner wherein said polymerase is used in the primer extension step of the PCR.

9. A method for selectively suppressing the amplification of a non-target nucleic acid fragment in a mixture of nucleic acid fragments, comprising the steps of:
    (a) attaching a first PCR suppression adapter to each end of a nucleic acid fragment in a first nucleic acid sample, and attaching a second PCR suppression adapter to each end of a nucleic acid fragment in a second nucleic acid sample;
    (b) combining said first and second nucleic acid samples to form said mixture of nucleic acid fragments;
    (c) denaturing and reannealing said nucleic acid fragments;

(d) contacting the nucleic acid mixture with a first nucleic acid primer comprising a nucleotide sequence that is complementary to a nucleotide sequence of said first adapter and contacting the nucleic acid mixture with a second nucleic acid primer comprising a nucleotide sequence that is complementary to a portion of the nucleotide sequence of said second adapter;

(e) adding to said mixture obtained after step (c) an effective amount of reagents necessary for performing a PCR; and (f) cycling the mixture obtained after step (e) through at least one cycle of the denaturing, annealing and primer extension steps of PCR wherein amplification of said non-target nucleic acid fragment is suppressed during PCR.

10. The method, according to claim 9, wherein step (e) further comprises filling in any single-stranded portions of said adapter after denaturing and reannealing of said nucleic acid fragments, wherein said adapter and said nucleic acid fragment comprise nucleic acid that is double-stranded.

11. A method for selectively suppressing the amplification of a non-target nucleic acid fragment in a mixture of nucleic acid fragments, comprising the steps of:

(a) dividing a nucleic acid sample into a first and a second nucleic acid sample;

(b) attaching a first PCR suppression adapter to each end of a nucleic acid fragment in said first nucleic acid sample and attaching a second PCR suppression adapter to each end of a nucleic acid fragment in said second nucleic acid sample;

(c) denaturing and reannealing said nucleic acid fragments;

(d) combining said first and second nucleic acid samples to form said mixture of nucleic acid fragments;

(e) contacting said nucleic acid mixture with a first nucleic acid primer comprising a nucleotide sequence that is complementary to a nucleotide sequence of said first adapter and contacting said nucleic acid mixture with said second nucleic acid comprising a nucleotide sequence that is complementary to a nucleotide sequence of said second adapter;

(f) adding to said mixture obtained after step (e) an effective amount of reagents necessary for performing a PCR; and (g) cychng the mixture obtained after step (f) through at least one cycle of the denaturing, annealing and primer extension steps of PCR wherein amplification of said non-target nucleic acid fragment is supressed during PCR.

12. The method, according to claim 11, wherein the reannealing reaction of step (c) is not allowed to proceed to completion.

13. The method, according to claim 11, wherein said first and second nucleic acid samples are each separately contacted with an excess of a third nucleic acid sample after performing step (b) but prior to performing step (c).

14. The method, according to claim 13, wherein said third nucleic acid sample comprises nucleic acid sequences that are complementary with at least one nucleic acid fragment in said first and second nucleic acid samples.

15. The method, according to claim 11, wherein step (c) further comprises filling in any single-stranded portions of said adapter after denaturing and reannealing of said nucleic acid fragments, wherein said adapter and said nucleic acid fragment comprise nucleic acid that is double-stranded.

* * * * *

UNITED STATES PATENT AND TRADEMARK OFFICE
CERTIFICATE OF CORRECTION

PATENT NO. : 5,565,340
DATED : October 15, 1996
INVENTOR(S) : Chenchik *et al.*

It is certified that error appears in the above-indentified patent and that said Letters Patent is hereby corrected as shown below:

Column 3: line 6: "transferring" should read --transferrin--; line 62: "T7-NotSffA." should read --T7-NotSrfA.--

Column 4: line 29: "primer." should read --primer TPA2.--

Column 11: line 57: "sheafing" should read --shearing--

Column 12: line 13: "an" should read --art--

Column 17: line 66: "transferfin" should read --transferrin--

Column 19: line 10: "Eppendoff microcentrffuge" should read --Eppendorf microcentrifuge--; line 12: "supematant" should read --supernatant--.

Column 21: line 24: "NotSff 4" should read --NotSrf 4--

Column 23: line 52: "0,002%" should read --0.002%--

Column 26: line 8: "Finnlear," should read --Finniear,--; line 29: "et aL" should read --et al.--

Column 37: lines 6&7: "to a portion of the nucleotide" should read --to a nucleotide--

UNITED STATES PATENT AND TRADEMARK OFFICE
CERTIFICATE OF CORRECTION

PATENT NO. : 5,565,340
DATED : October 15, 1996
INVENTOR(S) : Chenchik et al.

It is certified that error appears in the above-indentified patent and that said Letters Patent is hereby corrected as shown below:

Column 38: line 12: "cychng" should read --cycling--

Signed and Sealed this

Twenty-eighth Day of October, 1997

Attest:

Attesting Officer

BRUCE LEHMAN

Commissioner of Patents and Trademarks